(12) United States Patent
Smith et al.

(10) Patent No.: US 9,089,338 B2
(45) Date of Patent: Jul. 28, 2015

(54) MEDICAL DEVICE PACKAGING WITH WINDOW FOR INSERTION OF REUSABLE COMPONENT

(75) Inventors: Bret W. Smith, Kings Mills, OH (US); David N. Plescia, Cincinnati, OH (US); Michael J. Stokes, Cincinnati, OH (US); Sora Rhee, Cincinnati, OH (US); Timothy G. Dietz, Terrace Park, OH (US); Kevin D. Felder, Cincinnati, OH (US); Jeffrey L. Aldridge, Lebanon, OH (US); Emmanuel V. Tanghal, Lebanon, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 241 days.

(21) Appl. No.: 13/151,509

(22) Filed: Jun. 2, 2011

(65) Prior Publication Data
US 2012/0110824 A1    May 10, 2012

Related U.S. Application Data

(60) Provisional application No. 61/410,603, filed on Nov. 5, 2010, provisional application No. 61/487,846, filed on May 19, 2011.

(51) Int. Cl.
*B65D 85/00* (2006.01)
*A61B 18/14* (2006.01)
(Continued)

(52) U.S. Cl.
CPC ....... *A61B 18/1442* (2013.01); *A61B 17/00234* (2013.01); *A61B 17/320068* (2013.01);
(Continued)

(58) Field of Classification Search
CPC ........................... A61B 18/12; A61B 18/1442
USPC ......... 206/363, 438, 779, 569, 570, 571, 572, 206/634, 370, 305, 775
See application file for complete search history.

(56) References Cited

U.S. PATENT DOCUMENTS

| 1,754,806 A | 4/1930 | Stevenson |
|---|---|---|
| 3,297,192 A | 1/1967 | Swett |

(Continued)

FOREIGN PATENT DOCUMENTS

| DE | 102008051866 | 10/2010 |
|---|---|---|
| DE | 102009013034 | 10/2010 |

(Continued)

OTHER PUBLICATIONS

U.S. Appl. No. 12/576,776, filed Oct. 9, 2009, Boudreaux et al.
(Continued)

*Primary Examiner* — Steven A. Reynolds
(74) *Attorney, Agent, or Firm* — Frost Brown Todd LLC

(57) ABSTRACT

A system for inserting components into a medical device includes a container and an attachment member. The attachment member is coupled to a sidewall having an opening and is configured to be coupled to a medical device. Utilizing the attachment member and opening, an insertable component may be inserted into a medical device within the container while limiting the risk of contamination to the interior of the container. Alternatively, a cutting knob and an alignment member mounted to a container may be used. Cutting knob and alignment member are coupled and a knife on cutting knob is rotated about alignment member to create an opening in the container to access the interior of the medical device. Another alternative includes sandwiching an insertable component between an attachable member and the medical device while the attachable member and medical device are contained within flexible packaging that may be torn away.

11 Claims, 15 Drawing Sheets

(51) Int. Cl.
  *A61B 17/00* (2006.01)
  *A61B 17/32* (2006.01)
  *A61B 18/00* (2006.01)
  *A61B 18/04* (2006.01)
  *H02J 7/00* (2006.01)
  *H01M 2/26* (2006.01)
  *H01M 2/10* (2006.01)
  *A61B 18/12* (2006.01)
  *A61B 19/00* (2006.01)
  *A61B 17/064* (2006.01)
  *A61B 17/285* (2006.01)
  *A61B 17/29* (2006.01)

(52) U.S. Cl.
  CPC ......... *A61B17/320092* (2013.01); *A61B 18/00* (2013.01); *A61B 18/04* (2013.01); *A61B 18/12* (2013.01); *A61B 18/14* (2013.01); *A61B 18/1445* (2013.01); *H02J 7/0045* (2013.01); *A61B 17/064* (2013.01); *A61B 17/285* (2013.01); *A61B 18/1206* (2013.01); *A61B 18/1233* (2013.01); *A61B 19/38* (2013.01); *A61B 19/56* (2013.01); *A61B 2017/0046* (2013.01); *A61B 2017/00084* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/293* (2013.01); *A61B 2017/294* (2013.01); *A61B 2017/2929* (2013.01); *A61B 2017/2931* (2013.01); *A61B 2017/2933* (2013.01); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2019/4815* (2013.01); *A61B 2019/4868* (2013.01); *A61B 2019/4873* (2013.01); *H01M 2/10* (2013.01); *H01M 2/26* (2013.01); *Y10T 29/49005* (2015.01); *Y10T 29/49895* (2015.01); *Y10T 29/53913* (2015.01)

(56) References Cited

U.S. PATENT DOCUMENTS

| | | | |
|---|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden |
| 4,662,068 A | 5/1987 | Polonsky |
| 4,666,037 A | 5/1987 | Weissman |
| 4,685,459 A | 8/1987 | Koch et al. |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. et al. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,322,055 A | 6/1994 | Davison |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekunas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,531 A | 1/1997 | Liberti et al. |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,707,369 A | 1/1998 | Vaitekunas et al. |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,873,873 A | 2/1999 | Smith et al. |
| 5,882,310 A | 3/1999 | Marian, Jr. |
| 5,935,144 A | 8/1999 | Estabrook |
| 5,938,633 A | 8/1999 | Beaupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,083,223 A | 7/2000 | Baker |
| 6,099,537 A | 8/2000 | Sugai et al. |
| 6,113,593 A | 9/2000 | Tu et al. |
| 6,123,702 A | 9/2000 | Swanson et al. |
| 6,165,191 A | 12/2000 | Shibata et al. |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,287,304 B1 | 9/2001 | Eggers et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,609,414 B2 | 8/2003 | Mayer et al. |
| 6,622,731 B2 | 9/2003 | Daniel et al. |
| 6,623,500 B1 | 9/2003 | Cook et al. |
| 6,626,901 B1 | 9/2003 | Treat et al. |
| 6,647,281 B2 | 11/2003 | Morency |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,717,193 B2 | 4/2004 | Olewine et al. |
| 6,730,042 B2 | 5/2004 | Fulton et al. |
| 6,758,855 B2 | 7/2004 | Fulton, III et al. |
| 6,761,698 B2 | 7/2004 | Shibata et al. |
| 6,761,701 B2 | 7/2004 | Cucin |
| 6,783,524 B2 | 8/2004 | Anderson et al. |
| 6,815,206 B2 | 11/2004 | Lin et al. |
| 6,821,671 B2 | 11/2004 | Hinton et al. |
| 6,838,862 B2 | 1/2005 | Luu |
| 6,860,880 B2 | 3/2005 | Treat et al. |
| 6,869,435 B2 | 3/2005 | Blake |
| 6,923,807 B2 | 8/2005 | Ryan et al. |

(56) References Cited

U.S. PATENT DOCUMENTS

| | | |
|---|---|---|
| 6,982,696 B1 | 1/2006 | Shahoian |
| 7,031,155 B2 | 4/2006 | Sauciuc et al. |
| 7,077,853 B2 | 7/2006 | Kramer et al. |
| 7,083,589 B2 | 8/2006 | Banko et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckal et al. |
| 7,364,061 B2 | 4/2008 | Swayze et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,563,142 B1 | 7/2009 | Wenger et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,717,312 B2 | 5/2010 | Beetel |
| 7,721,936 B2 | 5/2010 | Shelton, IV et al. |
| 7,738,971 B2 | 6/2010 | Swayze et al. |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton et al. |
| 7,776,037 B2 | 8/2010 | Odom |
| 7,780,660 B2 | 8/2010 | Bourne et al. |
| 7,815,658 B2 | 10/2010 | Murakami |
| 7,845,537 B2 | 12/2010 | Shelton, IV et al. |
| 7,846,159 B2 | 12/2010 | Morrison et al. |
| 7,889,489 B2 * | 2/2011 | Richardson et al. ..... 361/679.32 |
| 7,922,063 B2 | 4/2011 | Zemlok et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Hideo et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,888 B2 | 10/2012 | Whitman |
| 8,298,253 B2 | 10/2012 | Charles |
| 8,301,262 B2 | 10/2012 | Mi et al. |
| 8,336,725 B2 | 12/2012 | Ramsey et al. |
| 8,344,690 B2 | 1/2013 | Smith et al. |
| 8,377,059 B2 | 2/2013 | Deville et al. |
| 8,400,108 B2 | 3/2013 | Powell et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz |
| 8,564,242 B2 | 10/2013 | Hansford et al. |
| 8,617,077 B2 | 12/2013 | van Groningen et al. |
| 8,641,629 B2 | 2/2014 | Kurokawa |
| 8,663,112 B2 | 3/2014 | Slayton et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 * | 9/2004 | Johnson et al. ............... 206/363 |
| 2005/0021065 A1 | 1/2005 | Yamada et al. |
| 2005/0033195 A1 | 2/2005 | Fulton, III et al. |
| 2005/0171522 A1 | 8/2005 | Christopherson |
| 2005/0256522 A1 | 11/2005 | Francischelli et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0084742 A1 * | 4/2007 | Miller et al. .................. 206/438 |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 * | 11/2007 | Sanderson .................... 206/320 |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2009/0030437 A1 | 1/2009 | Houser et al. |
| 2009/0043797 A1 | 2/2009 | Dorie et al. |
| 2009/0076506 A1 | 3/2009 | Baker |
| 2009/0105750 A1 | 4/2009 | Price et al. |
| 2009/0125026 A1 | 5/2009 | Rioux et al. |
| 2009/0137952 A1 | 5/2009 | Ramamurthy et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0209979 A1 | 8/2009 | Yates et al. |
| 2009/0209990 A1 | 8/2009 | Yates et al. |
| 2009/0240246 A1 | 9/2009 | Deville et al. |
| 2009/0253030 A1 | 10/2009 | Kooij |
| 2009/0264940 A1 | 10/2009 | Beale et al. |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 * | 1/2010 | Pittel et al. ................... 382/123 |
| 2010/0030218 A1 | 2/2010 | Prevost |
| 2010/0069940 A1 | 3/2010 | Miller et al. |

(56) References Cited

U.S. PATENT DOCUMENTS

| | | |
|---|---|---|
| 2010/0076455 A1 | 3/2010 | Birkenbach et al. |
| 2010/0089970 A1 | 4/2010 | Smith et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Alexander et al. |
| 2010/0211053 A1 | 8/2010 | Ross et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2010/0301095 A1 | 12/2010 | Shelton, IV et al. |
| 2011/0009694 A1 | 1/2011 | Schultz et al. |
| 2011/0015660 A1 | 1/2011 | Wiener et al. |
| 2011/0058982 A1 | 3/2011 | Kaneko |
| 2011/0077514 A1 | 3/2011 | Ulric et al. |
| 2011/0087218 A1 | 4/2011 | Boudreaux et al. |
| 2011/0152901 A1 | 6/2011 | Woodruff et al. |
| 2011/0224668 A1 | 9/2011 | Johnson et al. |
| 2011/0247952 A1* | 10/2011 | Hebach et al. ............ 206/320 |
| 2012/0179036 A1 | 7/2012 | Patrick et al. |
| 2012/0265230 A1 | 10/2012 | Laurent et al. |
| 2012/0283732 A1 | 11/2012 | Lam |
| 2012/0292367 A1 | 11/2012 | Morgan et al. |
| 2013/0085330 A1 | 4/2013 | Ramamurthy et al. |
| 2013/0085332 A1 | 4/2013 | Ramamurthy et al. |
| 2013/0085397 A1 | 4/2013 | Ramamurthy et al. |
| 2013/0090528 A1 | 4/2013 | Ramamurthy et al. |
| 2013/0090530 A1 | 4/2013 | Ramamurthy et al. |
| 2013/0090552 A1 | 4/2013 | Ramamurthy et al. |
| 2013/0116690 A1 | 5/2013 | Unger et al. |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| WO | WO 97/24072 | 7/1997 |
| WO | WO 00/65682 | 2/2000 |
| WO | WO 03/013374 | 2/2003 |
| WO | WO 03/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

U.S. Appl. No. 13/151,471, filed Jun. 2, 2011, Stulen et al.
U.S. Appl. No. 13/151,481, filed Jun. 2, 2011, Yates et al.
U.S. Appl. No. 13/151,488, filed Jun. 2, 2011, Shelton, IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,512, filed Jun. 2, 2011, Houser et al.
U.S. Appl. No. 13/151,515, filed Jun. 2, 2011, Felder et al.
International Search Report dated Jan. 26, 2012 for Application No. PCT/US11/059220.
International Search Report dated Feb. 1, 2012 for Application No. PCT/US11/059223.
International Search Report dated Jan. 12, 2012 for Application No. PCT/US11/059226.
International Search Report dated May 29, 2012 for Application No. PCT/US11/059358.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Feb. 28, 2013 for U.S. Appl. No. 13/270,667.
Office Action Non-Final dated Apr. 26, 2013 for U.S. Appl. No. 13/270,667.
Office Action Non-Final dated Dec. 21, 2012 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Non-Final dated Apr. 1, 2013 for U.S. Appl. No. 13/274,805.
Restriction Requirement dated Apr. 29, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
Office Action Non-Final dated Dec. 21, 2012 for U.S. Appl. No. 13/276,673.
Restriction Requirement dated Feb. 6, 2013 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
International Search Report and Written Opinion dated Jan. 26, 2012 for Application No. PCT/US2011/059212.

(56) References Cited

OTHER PUBLICATIONS

International Search Report and Written Opinion dated Feb. 2, 2012 for Application No. PCT/US2011/059378.
International Search Report dated Feb. 2, 2012 for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012 for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012 for Application No. PCT/US2011/059362.
Communication from International Searching Authority dated Feb. 2, 2012 for Application No. PCT/US2011/059222.
Communication from International Searching Authority dated Jan. 24, 2012 for Application No. PCT/US2011/059215.
Communication from International Searching Authority dated Feb. 2, 2012 for Application No. PCT/US2011/059378.
Machine Translation of the Abstract of German Application No. DE 102009013034.
Machine Translation of German Application No. DE 102008051866.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
International Search Report and Written Opinion dated Jul. 6, 2012 for PCT/US2011/059381.
Office Action Non-Final dated Aug. 6, 2013 for U.S. Appl. No. 13/151,471.
Notice of Allowance dated Dec. 6, 2013 for U.S. Appl. No. 13/151,471.
Restriction Requirement dated Jul. 5, 2013 for U.S. Appl. No. 13/151,488.
Office Action Non-Final dated Jun. 14, 2013 for U.S. Appl. No. 13/151,498.
Office Action Final dated 11/21/213 for U.S. Appl. No. 13/151,498.
Office Action Final dated Oct. 25, 2013 for U.S. Appl. No. 13/270,667.
Office Action Non-Final dated Nov. 21, 2013 for U.S. Appl. No. 13/271,352.
Office Action Final dated Aug. 16, 2013 for U.S. Appl. No. 13/274,516.
Office Action Non-Final dated Dec. 6, 2013 for U.S. Appl. No. 13/274,516.
Office Action Final dated Oct. 25, 2013 for Application No. US 13/274,540.
Office Action Final dated Sep. 12, 2013 for U.S. Appl. No. 13/274,805.
Office Action Non-Final dated Jun. 14, 2013 for U.S. Appl. No. 13/274,830.
Office Action Final dated Nov. 26, 2013 for U.S. Appl. No. 13/274,830.
Office Action Final dated Dec. 5, 2013 for U.S. Appl. No. 13/275,495.
Office Action Final dated Aug. 29, 2013 for U.S. Appl. No. 13/275,563.
Office Action Non-Final dated Aug. 19, 2013 for U.S. Appl. No. 13/276,673.
Office Action Non-Final dated Jun. 12, 2013 for U.S. Appl. No. 13/276,687.
Notice of Allowance dated Nov. 12, 2013 for U.S. Appl. No. 13/276,687.
Office Action Final dated Sep. 27, 2013 for U.S. Appl. No. 13/276,707.
Office Action Final dated Nov. 8, 2013 for U.S. Appl. No. 13/276,745.
Office Action Non-Final dated Mar. 28, 2014 for U.S. Appl. No. 13/151,471.
Office Action Non Final dated Mar. 18, 2014 for U.S. Appl. No. 13/151,498.
Office Action Non Final dated Jun. 18, 2014 for U.S. Appl. No. 13/151,503.
Restriction Requirement dated Jun. 11, 2014 for U.S. Appl. No. 13/151,512.
Office Action Non-Final dated Feb. 14, 2014 for U.S. Appl. No. 13/274,480.
Restriction Requirement dated Dec. 9, 2013 for U.S. Appl. No. 13/274,496.
Office Action Final dated May 15, 2014 for U.S. Appl. No. 13/274,496.
Office Action Non Final dated Feb. 6, 2014 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507
Office Action Final dated Jun. 12, 2014 for U.S. Appl. No. 13/274,516.
Office Action Non-Final dated Jan. 6, 2014 for U.S. Appl. No. 13/275,514.
Office Action Final dated Feb. 28, 2014 for U.S. Appl. No. 13/275,547.
Office Action Final dated Mar. 21, 2014 for U.S. Appl. No. 13/276,673.
Notice of Allowance dated Jun. 2, 2014 for U.S. Appl. No. 13/276,687.
Office Action Non-Final dated Feb. 28, 2014 for U.S. Appl. No. 13/276,745.

(56) References Cited

OTHER PUBLICATIONS

EP Communication dated Feb. 19, 2014 for Application No. EP 11781972.2.
International Preliminary Report on Patentability dated May 7, 2013 for Application No. PCT/US2011/059212.
International Preliminary Report on Patentability dated May 8, 2013 for Application No. PCT/US2011/059215.
International Preliminary Report on Patentability dated May 7, 2013 for Application No. PCT/US2011/059217.
International Preliminary Report on Patentability dated May 7, 2013 for Application No. PCY/US2011/059218.
International Preliminary Report on Patentability dated May 7, 2013 for Application No. PCT/US2011/059220.
International Preliminary Report on Patentability dated May 7, 2013 for Application No. PCT/US2011/059222.
International Preliminary Report on Patentability dated May 7, 2013 for Application No. PCT/US2011/059223.
International Preliminary Report on Patentability dated May 7, 2013 for Application No. PCT/US2011/059226.
International Preliminary Report on Patentability dated May 7, 2013 for Application No. PCT/US2011/059338.
International Preliminary Report on Patentability dated May 7, 2013 for Application No. PCT/US2011/059351.
International Preliminary Report on Patentability dated May 7, 2013 for Application No. PCT/US2011/059354.
International Preliminary Report on Patentability dated May 7, 2013 for Application No. PCT/US2011/059358.
International Preliminary Report on Patentability dated May 7, 2013 for Application No. PCT/US2011/059362.
International Preliminary Report on Patentability dated May 8, 2013 for Application No. PCT/US2011/059365.
International Preliminary Report on Patentability dated May 7, 2013 for Application No. PCT/US2011/059371.
International Preliminary Report on Patentability dated May 7, 2013 for Application No. PCT/US2011/059378.
International Preliminary Report on Patentability dated May 8, 2013 for Application No. PCT/US2011/059381.
US Office Action, Notice of Allowance, dated Aug. 19, 2014 for U.S. Appl. No. 13/151,471.
US Office Action, Notice of Allowance, dated Nov. 21, 2014 for U.S. Appl. No. 13/151,471.
US Office Action, Non-Final, dated Aug. 14, 2014 for U.S. Appl. No. 13/151,481.
US Office Action, Non-Final, dated Nov. 7, 2014 for U.S. Appl. No. 13/151,488.
US Office Action, Notice of Allowance, dated Aug. 6, 2014 for U.S. Appl. No. 13/151,498.
US Office Action, Notice of Allowance, dated Nov. 21, 2014 for U.S. Appl. No. 13/151,498.
US Office Action, Non-Final, dated Nov. 6, 2014 for U.S. Appl. No. 13/151,503.
US Office Action, Notice of Allowance, dated Oct. 29, 2014 for U.S. Appl. No. 13/151,512.
US Office Action, Restriction Requirement, dated Jul. 11, 2014 for U.S. Appl. No. 13/269,870.
US Office Action, Non-Final, dated Jan. 5, 2015 for U.S. Appl. No. 13/269,870.
US Office Action, Non-Final, dated Jul. 29, 2014 for U.S. Appl. No. 13/270,667.
US Office Action, Notice of Allowance, dated Dec. 17, 2014 for U.S. Appl. No. 13/270,667.
US Office Action, Restriction Requirement, dated Jul. 9, 2014 for U.S. Appl. No. 13/270,684.
US Office Action, Non-Final, dated Oct. 9, 2014 for U.S. Appl. No. 13/270,684.
US Office Action, Restriction Requirement, dated Sep. 11, 2014 for U.S. Appl. No. 13/270,701.
US Office Action, Non-Final, dated Dec. 16, 2014 for U.S. Appl. No. 13/270,701.
US Office Action, Restriction Requirement, dated Sep. 25, 2014 for U.S. Appl. No. 13/271,352.
US Office Action, Restriction Requirement, dated Oct. 2, 2013 for U.S. Appl. No. 13/274,480.
US Office Action, Final, dated Jul. 17, 2014 for U.S. Appl. No. 13/274,480.
US Office Action, Final, dated Aug. 22, 2014 for U.S. Appl. No. 13/274,496.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Notice of Allowance, dated Jan. 21, 2015 for U.S. Appl. No. 13/274,540.
US Office Action, Notice of Allowance, dated Nov. 28, 2014 for U.S. Appl. No. 13/274,805.
US Office Action, Notice of Allowance, dated Jan. 21, 2015 for U.S. Appl. No. 13/274,805.
US Office Action, Non-Final, dated Oct. 22, 2014 for U.S. Appl. No. 13/274,830.
US Office Action, Non-Final, dated Sep. 9, 2014 for U.S. Appl. No. 13/275,514.
US Office Action, Non-Final, dated Aug. 20, 2014 for U.S. Appl. No. 13/275,547.
US Office Action, Non-Final, dated Oct. 23, 2014 for U.S. Appl. No. 13/275,563.
US Office Action, Restriction Requirement, dated Jul. 9, 2014 for U.S. Appl. No. 13/276,660.
US Office Action, Non-Final, dated Aug. 14, 2014 for U.S. Appl. No. 13/276,673.
US Office Action, Notice of Allowance, dated Sep. 12, 2014 for U.S. Appl. No. 13/276,687.
US Office Action, Notice of Allowance, dated Dec. 23, 2014 for U.S. Appl. No. 13/276,687.
US Office Action, Non-Final, dated Aug. 20, 2014 for U.S. Appl. No. 13/276,725.
US Office Action, Notice of Allowance, dated Oct. 7, 2014 for U.S. Appl. No. 13/276,745.
US Office Action, Notice of Allowance, dated Dec. 19, 2014 for U.S. Appl. No. 13/276,745.
US Office Action, Restriction Requirement, dated Sep. 24, 2014 for U.S. Appl. No. 13/277,328.
US Office Action, Non-Final, dated Dec. 8, 2014 for U.S. Appl. No. 13/277,328.

* cited by examiner

MEDICAL DEVICE PACKAGING WITH WINDOW FOR INSERTION OF REUSABLE COMPONENT

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

A variety of packages exist for medical devices. In some instances, medical devices may be packaged in a single package with only some corresponding components included within a single container. Such single containers may be designed to maintain sterility of the medical device from the time of sterilization until the time for use by a medical professional. These containers may be generally constructed from materials such as plastic, high density polyethylene fiber material (such as Tyvek®), and others. Before and/or after the medical device is packaged, the medical device and package may be sterilized once prior to the use by a medical professional. Such sterilization methods may include gamma radiation, electron beam processing, x-ray radiation, or ultraviolet light irradiation, among other types. Some of these methods of sterilization may be incompatible with or cause damage to certain components within a medical device, such that different sterilization techniques may be warranted for different components of a medical device. In some such instances, a separate bulky support device may need to be provided to connect the component with the rest of the medical device before use.

With the advancement of the electronics industry, various medical devices that run at least partially on electrical power may be adapted to contain most, if not all, of the required components within the medical device. More specifically, some medical devices may be adapted to use an internal or attachable power source instead of requiring the device to be plugged into an external source by a cable. Other electronic components may also be adapted for insertion into medical device, such as a transducer or circuit board. Merely exemplary devices that may be adapted to include a portable power source and/or other integral electronic components are disclosed in U.S. Pat. No. 6,500,176 entitled "Electrosurgical Systems and Techniques for Sealing Tissue," issued Dec. 31, 2002, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; and U.S. Pub. No. 2010/0069940 entitled "Ultrasonic Device for Fingertip Control," published Mar. 18, 2010, the disclosure of which is incorporated by reference herein. Similarly, various ways in which medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

Electrically powered medical devices such as those referred to herein may require the use of high value or environmentally restricted disposable components to operate. The ability to reuse or reprocess these components over multiple uses may increase the value of the initial purchase by possibly spreading the cost of those components over the multiple uses. In addition or in the alternative, reclamation and reuse of the components may avoid or mitigate any environmental issues that may otherwise be associated with the disposal of the components after a single use. One potential approach may include reusing clean electrical components within multiple medical devices.

While several systems and methods have been made and used for packaging a medical device, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
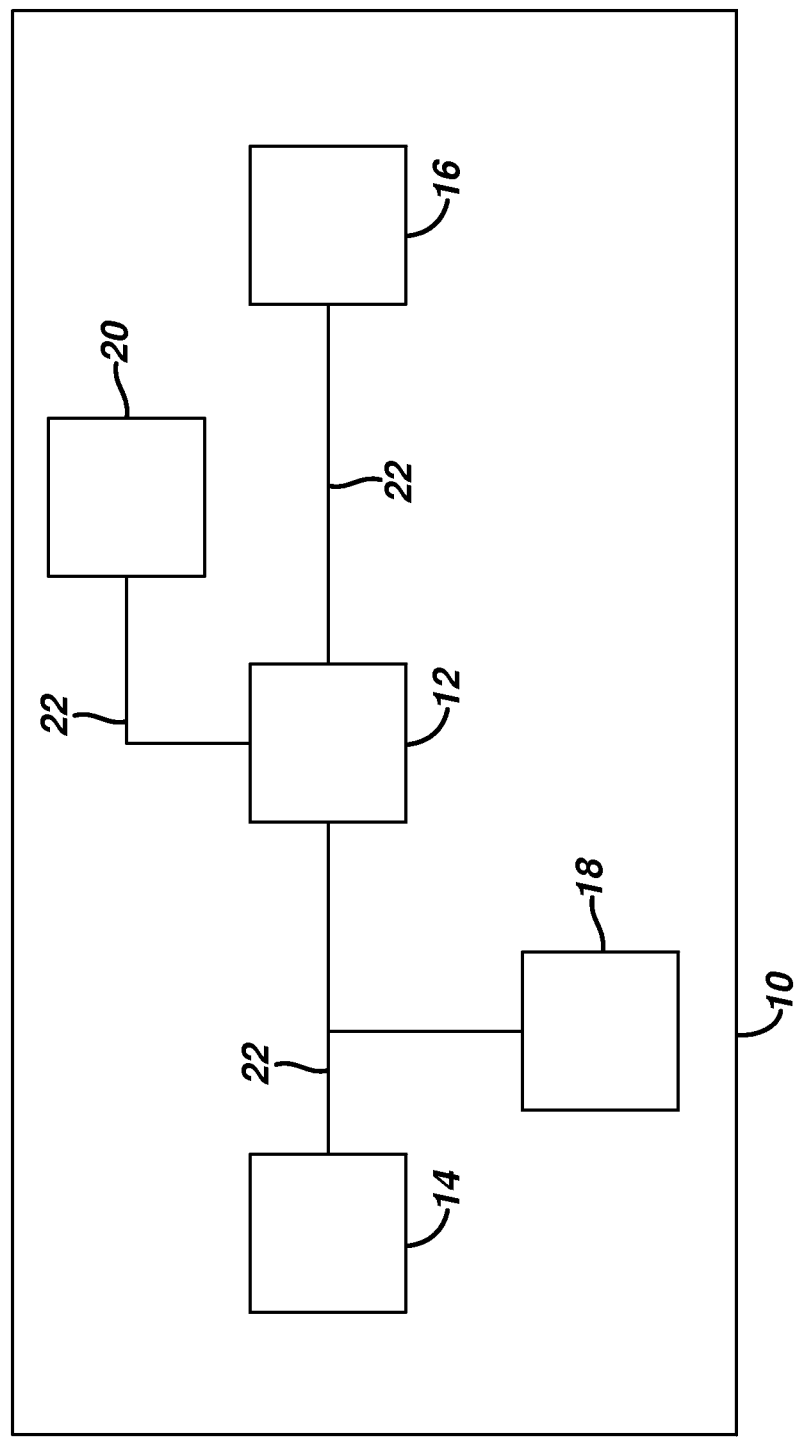
FIG. 1 depicts a schematic view of an exemplary medical device having an internal power source.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

I. Overview of Exemplary Medical Devices

FIG. 1 shows components of an exemplary medical device (10) in diagrammatic block form. As shown, medical device (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from medical device (10), which may further allow power source (14) to be readily recharged or reclaimed for resterilization and reuse, such as in accordance with the various teachings herein. In addition or in the alternative, control module (12) may be removed for servicing, testing, replacement, or any other purpose as will be apparent to one of ordinary skill in the art in view of the teachings herein.

End effector (16) is coupled to control module (12) by another electrical connection (22). End effector (16) is configured to perform a desired function of medical device (10). By way of example only, such function may include cauterizing tissue, ablating tissue, severing tissue, ultrasonically vibrating, stapling tissue, or any other desired task for medical device (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) may also be removable from medical device (10) for servicing, testing, replacement, or any other purpose as will be apparent to one of ordinary skill in the art in view of the teachings herein. In some versions, end effector (16) is modular such that medical device (10) may be used with different kinds of end effectors (e.g., as taught in U.S. Provisional Application Ser. No. 61/410,603, etc.). Various other configurations of end effector (16) may be provided for a variety of different functions depending upon the purpose of medical device (10) as will be apparent to those of ordinary skill in the art in view of the teachings herein. Similarly, other types of components of a medical device (10) that may receive power from power source (14) will be apparent to those of ordinary skill in the art in view of the teachings herein.

Medical device (10) of the present example includes a trigger (18) and a sensor (20), though it should be understood that such components are merely optional. Trigger (18) is coupled to control module (12) and power source (14) by electrical connection (22). Trigger (18) may be configured to selectively provide power from power source (14) to end effector (16) (and/or to some other component of medical device (10)) to activate medical device (10) when performing a procedure. Sensor (20) is also coupled to control module (12) by an electrical connection (22) and may be configured to provide a variety of information to control module (12) during a procedure. By way of example only, such configurations may include sensing a temperature at end effector (16) or determining the oscillation rate of end effector (16). Data from sensor (20) may be processed by control module (12) to effect the delivery of power to end effector (16) (e.g., in a feedback loop, etc.). Various other configurations of sensor (20) may be provided depending upon the purpose of medical device (10) as will be apparent to those of ordinary skill in the art in view of the teachings herein. Of course, as with other components described herein, medical device (10) may have more than one sensor (20), or sensor (20) may simply be omitted if desired.

Figure 2:
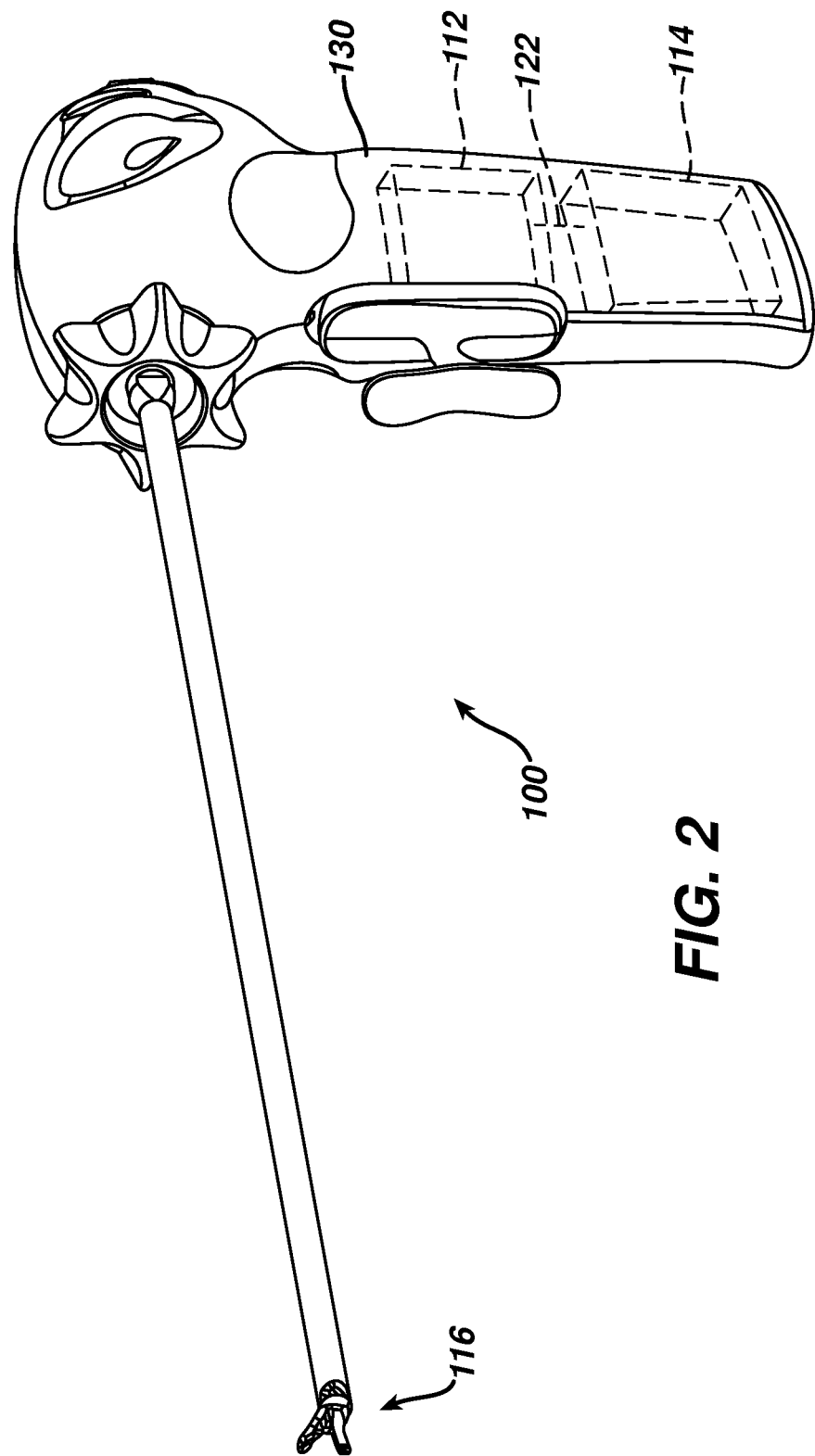
FIG. 2 depicts a perspective view of an exemplary medical device having an internal power source.

FIG. 2 depicts a merely exemplary form that medical device (10) may take. In particular, FIG. 2 shows a medical device (100) comprising a power source (114), a control module (112), a housing (130), end effector (116), and an electrical connection (122). In the present example, power source (114) is located internally within housing (130) of medical device (100). Alternatively, power source (114) may only partially extend into housing (130) and may be selectively attachable to a portion of housing (130). In yet a further exemplary configuration, a portion of housing (130) may extend into power source (114) and power source (114) may be selectively attachable to the portion of housing (130). Power source (114) may also be configured to detach from medical device (100) and decouple from control module (112) or electrical connection (150). As a result, power source (114) may be completely separated from medical device (100) in some versions. As is readily apparent, this may allow the power source (114) to be removed to be recharged or reclaimed for resterilization and reuse, such as in accordance with various teachings herein. After recharging, or after an initial charge, power source (114) may be inserted or reinserted into medical device (100) and secured to housing (130) or internally within housing (130). Of course, medical device (100) may also allow power source (114) to be charged and/or recharged while power source (114) is still in or otherwise coupled relative to housing (130).

It should also be understood that control module (112) may be removed for servicing, testing, replacement, or any other purpose as will be apparent to one of ordinary skill in the art in view of the teachings herein. Further, end effector (116) may also be removable from medical device (100) for servicing, testing, replacement, or any other purpose as will be apparent to one of ordinary skill in the art in view of the teachings herein. While certain configurations of an exemplary medical device (100) have been described, various other ways in which medical device (100) may be configured will be apparent to those of ordinary skill in the art in view of the teachings herein. By way of example only, medical devices (10, 100) and/or any other medical device referred to herein may be constructed in accordance with at least some of the teachings of U.S. Pat. Nos. 6,500,176; 7,416,101; 7,738,971; U.S. Pub. No. 2006/0079874; U.S. Pub. No. 2007/0191713; U.S. Pub. No. 2007/0282333; U.S. Pub. No. 2008/0200940; U.S. Pub. No. 2009/0209990, issued as U.S. Pat. No. 8,657, 174 on Feb. 25, 2014; U.S. Pub. No. 2010/0069940; and/or U.S. Provisional Application Ser. No. 61/410,603.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that various teachings herein may be readily combined with various teachings in any of the following patent applications, all of which are filed on even date herewith and the disclosures of all of which are incorporated by reference herein: U.S. patent application Ser. No. 13/151,471, issued as U.S. Pat. No. 9,000,720 on Apr. 7, 2015, entitled "Medical Device Packaging with Charging Interface"; U.S. patent application Ser. No. 13/151,481, published as U.S. Pub. No. 2012/0116379 on May 10, 2012, entitled "Motor Driven Electrosurgical Device with Mechanical and Electrical Feedback"; U.S. patent application Ser. No. 13/151,488, published as U.S. Pub. No. 2012/0111591 on May 10, 2012, entitled "Packaging for Reclaimable Component of a Medical Device"; U.S. patent application Ser. No. 13/151,498, now U.S. Pat. No. 9,017,851, issued on Apr. 28, 2015 Pub. No. 2012/0115007, entitled "Sterile Housing for Non-Sterile Medical Device Component"; U.S. patent application Ser. No. 13/151,503, published as U.S. Pub. No. 2012/0116380 on May 10, 2012, entitled "Sterile Medical Instrument Charging Device"; U.S. patent application Ser. No. 13/151,512, published as U.S. Pub. No. 2012/0110810 on May 10, 2012, entitled "Medical Device with Feature for Sterile Acceptance of Non-Sterile Reusable Component"; and U.S. patent application Ser. No 13/151,515, published as U.S. Pub. No. 2012/0305427 on Dec. 6, 2012, entitled "Sterile Package System for Medical Device." Various suitable ways in which teachings herein may be combined with teachings of the above-referenced patent applications, as well as various ways in which teachings of the above-referenced patent applications may be combined together with or without teachings herein, will be apparent to those of ordinary skill in the art.

II. Non-Sterile Component Insertion Utilizing a Through Hole in the Sterile Package For medical devices utilizing recoverable components, the ability to reuse those components over multiple uses may increase the value of the initial purchase by possibly spreading the cost of those components over the multiple uses. In addition or in the alternative, if environmental restrictions limit the disposal of certain components, the ability to remove those components from the device may permit the shipping of those components back to a manufacturer for recycling or proper disposal. One approach for insertion and removal of components may include reusing clean components within multiple devices by inserting the components into a medical device while the medical device is still within a sterile environment. Additionally, access for insertion of the clean components may be limited to the interior of a medical device, thereby limiting any potential contamination of the sterile exterior of the medical device. The following examples relate to various illustrative ways in which non-sterile components may be inserted into medical devices while maintaining the sterility of the exterior of the medical device, though other examples and variations of the following teachings will be apparent to those of ordinary skill in the art in view of the teachings herein.

A. Medical Device, Sterile Insertion Package, and Threaded Cap

Figure 3:
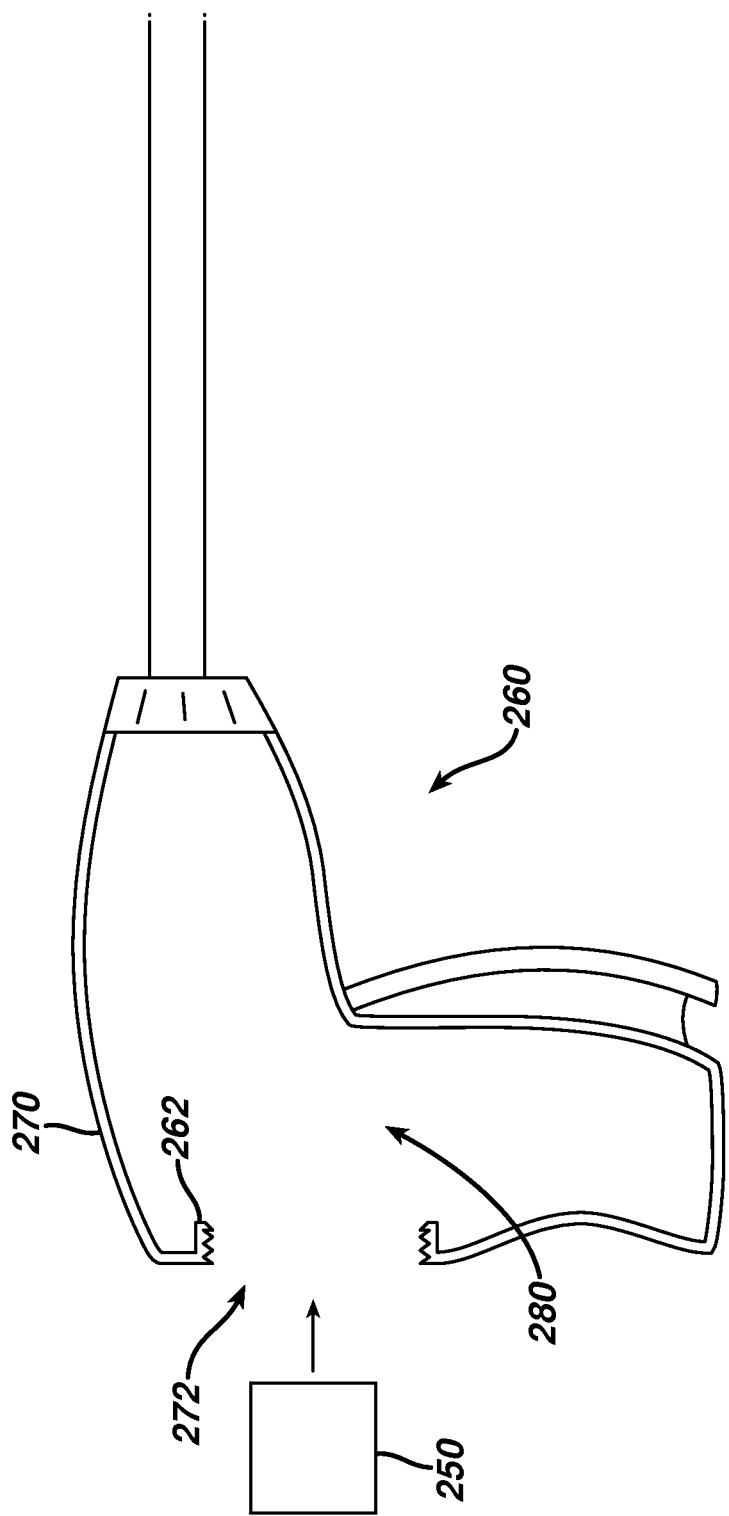
FIG. 3 depicts a partial side cross-sectional view of an exemplary medical device having a through hole for insertion of a non-sterile insertable component into a medical device.

One merely exemplary configuration to provide insertion of non-sterile components into a sterile medical device may include a sterile insertion package, a medical device having an interior cavity for an insertable component, and a threaded cap to seal the medical device once the insertable component is inserted into the medical device. For instance, FIG. 3 shows an exemplary medical device (260) that may be constructed in accordance with at least some of the teachings of medical device (10) or medical device (100) as previously referred to herein, though it should be understood that medical device (260) may have any other suitable configuration as will be apparent to one of ordinary skill in the art in view of the teachings herein. In the present example, medical device (260) comprises a housing (270). Housing (270) at least partially defines an interior cavity (280) that is configured to receive an insertable component (250). By way of example only, insertable component (250) may comprise a power source, such as one of the types of batteries previously discussed herein, a plurality of batteries in the form of a battery pack, a printed circuit board, a transducer, and/or any other insertable component or combination of components as will be apparent to those of ordinary skill in the art in view of the teachings herein. Interior cavity (280) of exemplary medical device (260) is shown as a substantially open cavity within medical device (260); however, it should be understood that interior cavity (280) may be sized to accommodate only insertable component (250), a plurality of various insertable components (250), and/or any other suitable configuration for interior cavity (280) as will be apparent to one of ordinary skill in the art in light of the teachings herein. Housing (270) may be made from a variety of materials including plastics, polyethylene terephthalate glycol (or PETG), thermoplastic polymer resins, and/or any other suitable rigid material for the housing of medical device (260). Various other materials and configurations for housing (270) may be provided as will be apparent to those of ordinary skill in the art in view of the teachings herein.

Housing (270) of medical device (260) of the present example further comprises a housing opening (272) sized to permit the passage of insertable component (250) through housing opening (272) and into the interior cavity (280) of medical device (260). In the example depicted, housing opening (272) is a circular opening; however, it should be understood that housing opening (272) may take a variety of geometrical configurations including rectangular, square, triangular, hexagonal, or any other configuration suitable for insertion of insertable component (250) into medical device (260) as will be apparent to one of ordinary skill in the art in light of the teachings herein. Housing opening (272) of the present example is located on a rear surface of medical device (260), though it should be understood that housing opening (272) may be located at a variety of locations on housing (270) including the side, front, bottom, or top surfaces of housing (270) or any other suitable location as will be apparent to those of ordinary skill in the art in light of the teachings herein. Housing (270) of the present example further comprises device threading (262) encircling the perimeter of housing opening (272). Device threading (262) is configured to complement threading (232) of flanged bushing (230), as will be described later herein. It should be understood that device threading (262) is merely optional and other attachment configurations may be used to attach medical device (260) to flanged bushing (230), such as resilient snap-on members, break-away tabs, bayonet mount features, or other suitable attachment configurations as will be readily apparent to one of ordinary skill in the art in view of the teachings herein. Various other configurations for housing opening (272) and/or device threading (262) may be provided as will be apparent to those of ordinary skill in the art in view of the teachings herein.

Figure 4:
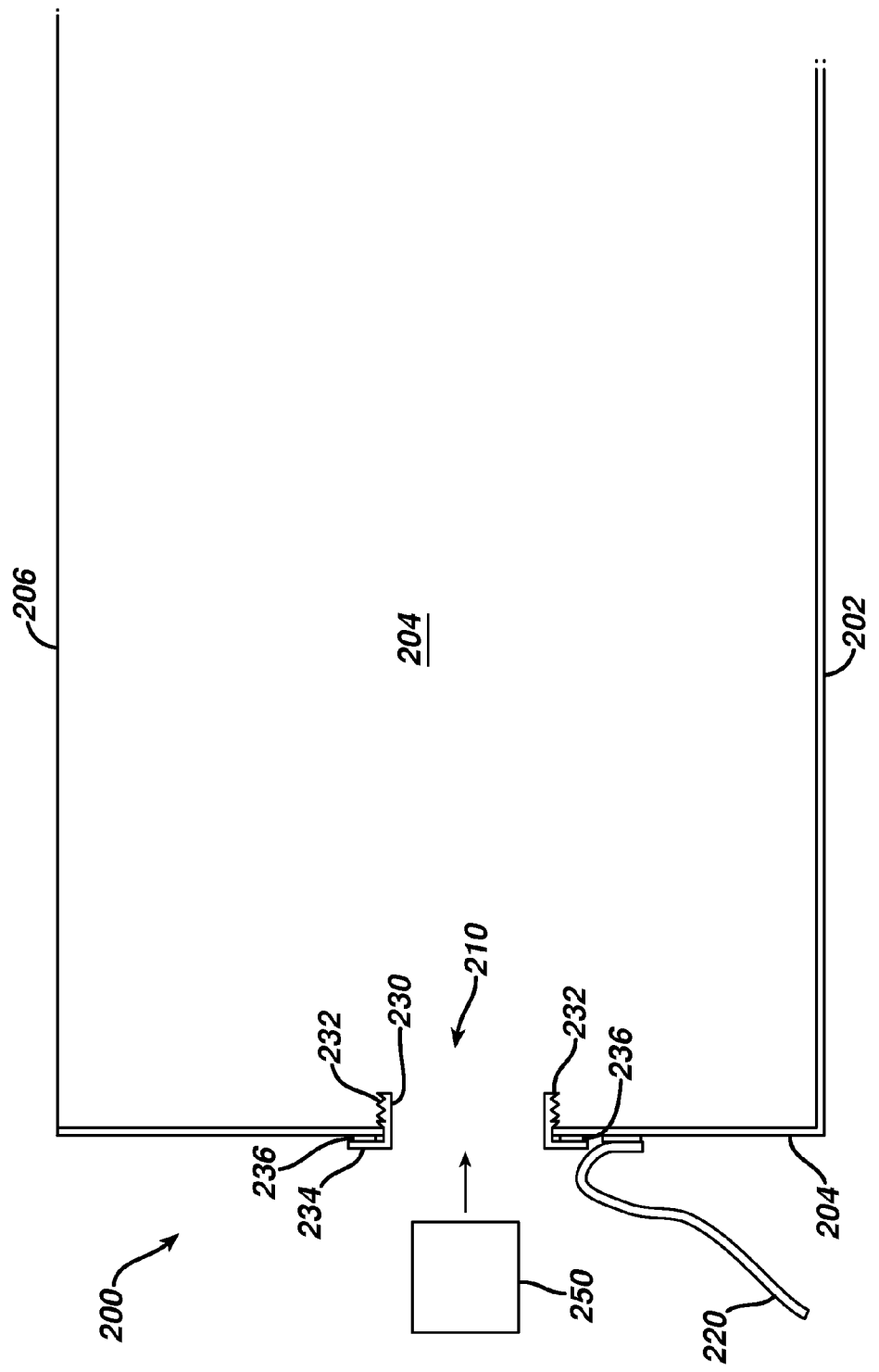
FIG. 4 depicts a partial side cross-sectional view of an exemplary medical device package having an opening for insertion of a non-sterile insertable component.

FIG. 4 shows a partial side cross-sectional view of an exemplary insertion package (200) for inserting insertable component (250) into a medical device, such as medical device (260) of FIG. 3 described herein. For instance, medical device (260) may be packaged within package (200) for shipment and storage, maintaining the sterility of medical device (260) the whole time, with package (200) being opened to retrieve medical device (260) right before medical device (260) is to be used in a medical procedure. Insertion package (200) of this example comprises a base (202), a plurality of sidewalls (204), and a cover (206). In some versions, package (200) is formed as a blister pack. In the present example, base (202) and sidewalls (204) comprise a single homogeneous continuum of material and may be made from a variety of materials including plastics, polyethylene terephthalate glycol (or PETG), other thermoplastic polymer resins, or any other suitable rigid or semi-rigid material to maintain sterility. Cover (206) may also be made from a variety of materials including plastics, plastic peelable films, high density polyethylene fiber materials (such as Tyvek® of E. I. du Pont de Nemours and Company of Wilmington, Del.), or any other suitable material to maintain sterility. Cover (206) of the present example is adhesively attached to sidewalls (204) to seal insertion package (200). Cover (206) may alternatively be attached by mechanical attachment such as a snap-on lid, screw-on lid, or friction fit lid. Yet another method of attachment for cover (206) may comprise heat sealing cover (206) to sidewalls (204). Various other configurations of insertion package (200) and attachment methods for attaching cover (206) to insertion package (200) may be provided as will be apparent to those of ordinary skill in the art in view of the teachings herein.

Insertion package (200) further comprises at least one package opening (210) in at least one of the sidewalls (204). In the present example, package opening (210) is sized to allow the passage of insertable component (250) through package opening (210) and into the interior of a medical device, such as into interior cavity (280) of medical device (260) of FIG. 3 or into any other suitable cavity of a medical device as will be apparent to one of ordinary skill in the art in light of the teachings herein. In the present example, package opening (210) is a circular opening corresponding to and similarly sized to housing opening (272); however, it should be understood that package opening (210) may take a variety of geometrical configurations including rectangular, square, triangular, hexagonal, or any other configuration suitable to permit insertion of insertable component (250) as will be apparent to one of ordinary skill in the art in light of the teachings herein.

Insertion package (200) of the present example further comprises a removable cover (220), though it should be understood that this component is merely optional. Removable cover (220) may be made from a variety of materials including plastics, plastic peelable films, high density polyethylene fiber materials (such as Tyvek®), or any other suitable material to maintain sterility. Removable cover (220) is sized and configured to seal package opening (210). By way of example only, cover (220) of the present example is attached by an adhesive, such as cyanoacrylate or epoxy, to sidewall (204) of insertion package (200) to cover package opening (210). Alternatively, cover (220) may be configured to mechanically attach to sidewall (204), such as by snapping-on to a rim (not shown) protruding from sidewall (204). Cover (220) may alternatively be configured to mechanically attach to flanged bushing (230), as will be described herein. Exemplary mechanical attachments to flanged bushing (230) may include threading onto flanged bushing (230), snapping onto flanged bushing (230), or any other suitable mechanical attachment to flanged bushing (230) as will be apparent to one of ordinary skill in the art in view of the teachings herein. In yet a further exemplary configuration, opening cover (220) may be heat sealed to sidewall (204) of insertion package (200) or to flanged bushing (230). Various other materials for opening cover (220) and other suitable ways to attach opening cover (220) to selectively close package opening (210) may be provided as will be apparent to those of ordinary skill in the art in view of the teachings herein.

In the present example, insertion package (200) further comprises a flanged bushing (230). Flanged bushing (230) is sized and configured to be inserted into package opening (210). In the present example, flanged bushing (230) comprises a cylindrical portion that has an open central channel and that is sized to fit within package opening (210) of sidewall (204). Flanged bushing (230) further comprises an exterior rim (234) and threading (232), though it should be understood that these features are merely optional. Exterior rim (234) of the present example is formed as a flange that extends outwardly from the cylindrical portion and that is configured to restrict flanged bushing (230) from passing entirely through package opening (210) by abutting against the exterior surface of sidewall (204) when flanged bushing (230) is inserted. In the current configuration, exterior rim (234) is a single continuous homogeneous protrusion from flanged bushing (230); however, it should be understood that exterior rim (234) may alternatively comprise a plurality of protrusions or that exterior rim (234) may comprise a separate component that may be coupled to flanged bushing (230). Exterior rim (234) may further be secured to sidewall (204) once flanged bushing (230) is inserted. One such exemplary attachment comprises adhesively coupling exterior rim (234) to sidewall (204). An alternative attachment comprises mechanically attaching exterior rim (234) to sidewall (204), such as by rivets, a snap-on connection, or any other suitable mechanical attachment.

Threading (232) of flanged bushing (230) complements device threading (262) in the present example, though it should be understood that threading (232) is merely optional. Other suitable attachment configurations, as noted previously herein, may be used to attach medical device (260) to flanged bushing (230), such as resilient snap-on members, break-away tabs, or other suitable attachment configurations as will be readily apparent to one of ordinary skill in the art in view of the teachings herein. When inserted into package opening (210), exterior rim (234) of the present exemplary flanged bushing (230) abuts against the exterior surface of sidewall (204) to prevent flanged bushing (230) from completely passing through package opening (210) while permitting a portion of flanged bushing (230), including threading (232), to project into the interior of insertion package (200). Flanged bushing (230) may be made from a variety of materials including plastics, polyethylene terephthalate glycol (or PETG), other thermoplastic polymer resins, or any other suitable rigid or semi-rigid material. Various other materials for flanged bushing (230) and other suitable configurations for flanged bushing (230) may be provided as will be apparent to one of ordinary skill in the art in view of the teachings herein.

Flanged bushing (230) of the present example further comprises a first seal (236), though it should be understood that this component is merely optional. First seal (236) is sized to substantially conform to the size and shape of exterior rim (234) and may be attached to the surface of exterior rim (234) abutting sidewall (204) of insertion package (200). First seal (236) may be made from a variety of materials, including natural rubber, silicone, neoprene, Polytetrafluoroethylene (or PTFE), or other suitable sealing materials as will be apparent to those of ordinary skill in the art in view of the teachings herein. In the present example, first seal (236) is an o-ring type seal that fits around flanged bushing (230). When flanged bushing (230) of the present example is inserted into package opening (210) of sidewall (204) and coupled to a medical device, such as medical device (260) of FIG. 3, exterior rim (234) compresses first seal (236) to hermetically seal flanged bushing (230) to sidewall (204). Alternatively, if exterior rim (234) is configured to be secured to sidewall (204), the attachment of exterior rim (234) to sidewall (204) may compress first seal (236) to hermetically seal flanged bushing (230) to sidewall (204). It should be understood that a second seal (not shown) may also be provided between the medical device and the interior of sidewall (204). This may be done in the alternative to first seal (234) or in addition to first seal (236) to further seal flanged bushing (230) to sidewall (204). The second seal may also be an o-ring type seal configured in a similar fashion to first seal (236). Various other suitable configurations for first seal (234) and flanged bushing (230) may be provided as will be apparent to one of ordinary skill in the art in view of the teachings herein.

Figure 5:
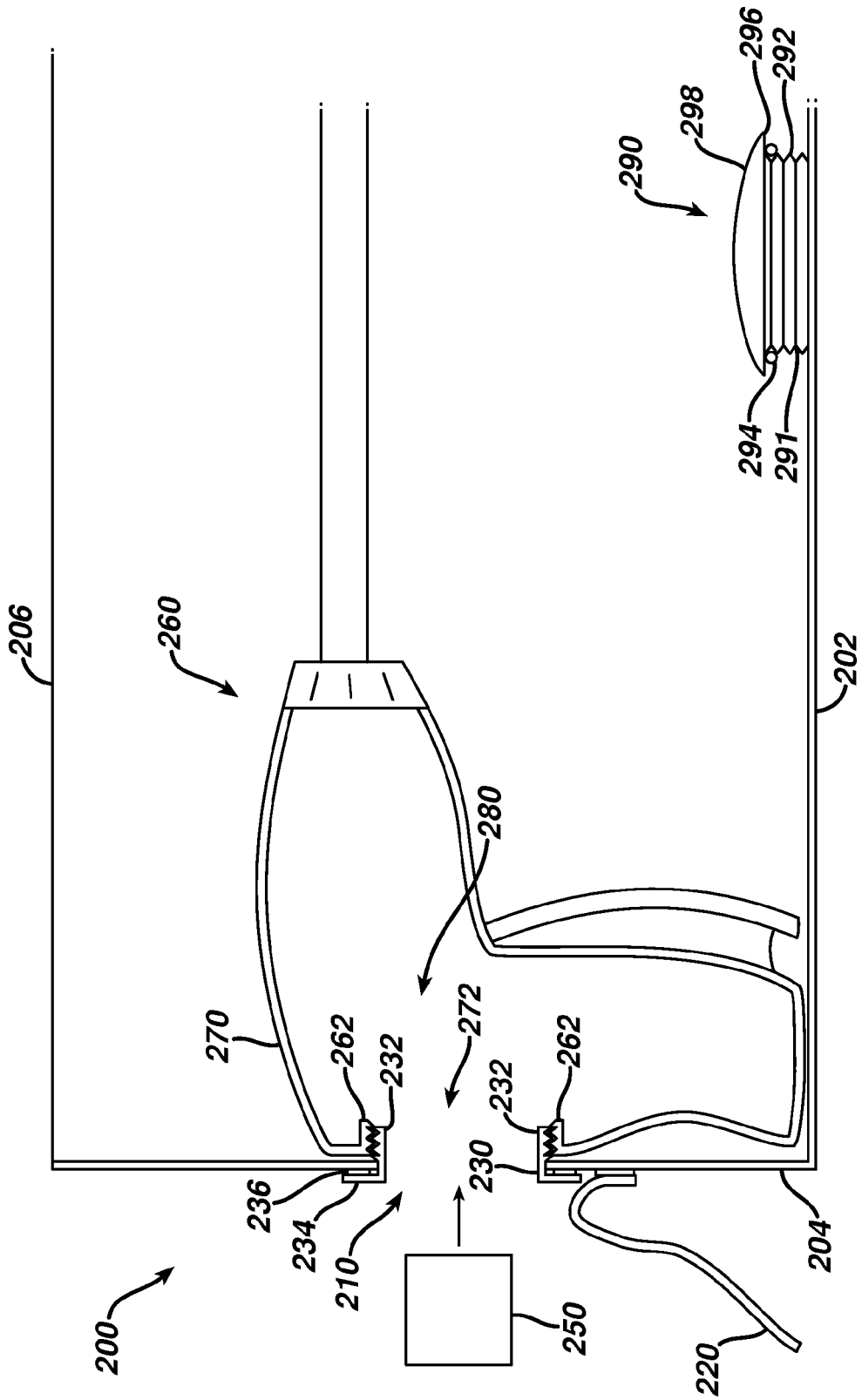
FIG. 5 depicts a partial side cross-sectional view of the exemplary medical device of FIG. 3 coupled to the exemplary package of FIG. 4 for inserting a non-sterile insertable component.

FIG. 5 depicts medical device (260) of FIG. 3 inserted into and couple to insertion package (200) of FIG. 4. FIG. 5 further depicts a cap (290) for sealing medical device (260) once insertable component (250) is inserted into interior cavity (280) of medical device (260). Cap (290) is sized and configured to seal housing opening (272) of medical device (260) when cap (290) is coupled to housing (270). Cap (290) may be made from a variety of materials including plastics, PETG, thermoplastic polymer resins, or any other suitable rigid material for use with cap (290) as will be apparent to one of ordinary skill in the art in light of the teachings herein.

Cap (290) of the present example comprises a cap body (291), a distal surface (298), a ledge (296), cap threading (292), and a cap seal (294), though it should be understood that ledge (296), cap threading (292), and cap seal (294) are merely optional components. Cap body (291) and distal surface (298) are sized and configured such that when cap (290) is inserted into housing opening (272), cap (290) substantially seals interior cavity (280) of medical device (260). In the present example, cap body (291) is cylindrical in shape and is configured to correspond to housing opening (272), though it should be understood that cap body (291) may be any other geometric shape corresponding to housing opening (272) as will be apparent to those of ordinary skill in the art in light of the teachings herein. Cap body (291) of the present example comprises cap threading (292) on the exterior surface of cap body (291). Cap threading (292) is configured to complement threading (262) of medical device (260). It should be understood that cap (290) may alternatively be coupled to medical device (260) through a variety of other suitable configurations, including mechanical attachments such as snap-on or friction fit attachment, adhesive attachment, or by any other suitable attachment method as will be apparent to those of ordinary skill in the art in view of the teachings herein.

In the present example, ledge (296) protrudes outwardly and perpendicular to the surface of cap body (291) and is located distally of cap threading (292). Ledge (296) may alternatively be at a variety of angles from cap body (291) suitable for coupling cap (290) to housing (270) as will be apparent to one of ordinary skill in the art in light of the teachings herein. Cap seal (294) is sized and configured to substantially conform to ledge (296). In the present example, cap seal (294) is an o-ring type seal. Cap seal (294) is configured such that when cap (290) is coupled to medical device (260), cap seal (294) hermetically seals cap (290) with housing (270), thereby preventing fluid transfer into or out of interior cavity (280) of medical device (260). Cap seal (294) may be made from a variety of materials, including natural rubber, silicone, neoprene, Polytetrafluoroethylene (or PTFE), or other suitable sealing materials and may be configured according to other suitable configurations as will be apparent to those of ordinary skill in the art in view of the teachings herein. Cap (290) remains within package (200) along with medical device (260) during transport and storage, such that cap (290) remains sterile before medical device (260) is used in a medical procedure.

For the initial assembly of exemplary insertion package (200) with medical device (260), medical device (260) is first coupled to flanged bushing (230). In the present example, device threading (262) of medical device (260) is coupled to threading (232) on flanged bushing (230). In some versions, flanged bushing (230) is rotatable relative to insertion package (200), allowing flanged bushing to be secured to medical device (260) by rotating flanged bushing (230) relative to package (200) and relative to medical device (260) while those two components remain stationary. In addition or in the alternative, medical device (260) may be rotatable relative to package, allowing flanged bushing to be secured to medical device (260) by rotating medical device (260) relative to package (200) and relative to flanged bushing (230) while those two components remain stationary.

When flanged bushing (230) and medical device (260) are coupled together, the rear surface of medical device (260) and exterior rim (234) of flanged bushing (230) cooperatively compress against both the interior and exterior surfaces of sidewall (204). As a result, first seal (236) is compressed between exterior rim (234) and the exterior surface of sidewall (204) to form a hermetic seal. If a second seal is provided, second seal may be compressed by the rear surface of housing (270) of medical device (260) and the interior surface of sidewall (204) to additionally or alternatively form a hermetic seal. Once sealed, objects may pass only through flanged bushing (230) into interior cavity (280) of medical device (260). Thus, the sterility within the sealed insertion package (200) and the sterility of the exterior of medical device (260) may be maintained even while the interior cavity (280) of medical device (260) is exposed to the environment. Cap (290) may be secured to base (202) within insertion package (200) or be simply placed within insertion package (200). Cover (206) is then attached to sidewalls (204) to seal insertion package (200) with medical device (260) and cap (290) contained therein. Opening cover (220) is then attached to sidewall (204) to seal off flanged bushing (230) and interior cavity (280) of medical device (260). Opening cover (220) of the present example is adhesively attached to sidewall (204). Once medical device (260) and cap (290) are contained within insertion package (200), and cover (206) and opening cover (220) are attached, insertion package (200) is in a ready-to-use state, such that the entire assembly may be shipped and stored in non-sterile environments while still maintaining sterility of the contents of package (200). Other various suitable arrangements and assemblies for insertion package (200) containing a medical device will be apparent to those of ordinary skill in the art in view of the teachings herein.

Insertion package (200), including medical device (260) and cap (290), may be sterilized after package (200) is sealed. In one exemplary sterilization technique, insertion package (200) is placed in a field of radiation that can penetrate insertion package (200), such as gamma radiation, x-rays, or high-energy electrons. The radiation may kill bacteria on medical device (260), on cap (290), and within insertion package (200). Insertion package (200), medical device (260), and cap (290) may also be sterilized using any other technique known in the art, including but not limited to beta or gamma radiation, ethylene oxide, electron beam sterilization, or steam. The sterilized insertion package (200) containing medical device (260) and cap (290) may then be stored or shipped to a medical facility for use. Of course, one or more components of medical device (260) and/or cap (290) may be sterilized before being put in insertion package (200), before insertable component (250) is inserted into medical device (260), and/or before package (200) is sealed shut.

Once a user wants to utilize medical device (260), the user initially detaches opening cover (220) of the present example to expose only interior cavity (280) to insert insertable component (250), as shown in FIG. 5. When opening cover (220) is opened, flanged bushing (230) coupled to medical device (260) may prevent contamination of the interior of insertion package (200) by limiting access to only interior cavity (280) of medical device (260). If first seal (234) is included, first seal (234) may cooperate with flanged bushing (230) to further maintain the sterility within insertion package (200) while inserting insertable component (250). In yet a further configuration, second seal (not shown) may further maintain sterility within insertion package (200) by providing a second seal located between housing (270) of medical device (260) and the interior surface of sidewall (204). Use of flanged bushing (230) may permit non-sterilized components to be used and/or reused within a medical device by reducing the risk of contamination of the interior of insertion package (200) and the exterior of sterilized medical device (260) contained within package (200). Flanged bushing (230) may alternatively permit insertion of sterilized components within medical device (260). Once insertable component (250) is inserted within interior cavity (280) of medical device (260), opening cover (220) may be resealed over flanged bushing (230), though it should be understood this step is merely optional.

Following the insertion of insertable component (250) into medical device (260), cover (206) is then detached to expose medical device (260) within insertion package (200). Medical device (260) of the present example is then unscrewed from threading (232) of flanged bushing (230) for use. As alluded to above, this may entail rotating flanged bushing (236) relative to package (200) and relative to medical device (260); rotating medical device (260) relative to flanged bushing (236) and relative to package (200); and/or using any other suitable technique. If alternative coupling components or attachments are used, as previously described herein, the appropriate decoupling or detachment may be done, such as breaking away a break-away attachment or unsnapping a snap-on attachment, as will be apparent to those of ordinary skill in the art in view of the teachings herein. Once medical device (260) is detached, cap (290) may be detached from base (202), if attached thereto, or be simply removed from insertion package (200) for coupling with medical device (260). In the present example, cap (290) is threaded into housing opening (272) by threading cap threading (292) into device threading (262). Optional cap seal (296) may be compressed by ledge (296) when attaching cap (290) to medical device (260) to seal interior cavity (280) of medical device (260) to prevent potential fluid transfer or contamination of insertable component (250) and interior cavity (280) of medical device (260). Medical device (260) may then be used to perform a medical operation.

After medical device (260) has been used, a user may remove cap (290) to allow removal of insertable component (250) from medical device (260) (e.g., by dumping insertable component (250) from medical device (260), by ejecting insertable component (250) from medical device (260), etc.). The used insertable component (250) may then be disposed of, reprocessed, recharged, or otherwise be handled. Furthermore, the used insertable component (250) may be inserted into another medical device (260) through another package (200) and flanged bushing (230), either with or without further processing of insertable component between use of insertable component (250) in a first medical device (260) and a second medical device (260). It should therefore be understood that the presence of openings (210, 272) and the use of flanged bushing (230) may facilitate the use of the same insertable component (250) in several different medical devices (260), without insertable component (250) having to be re-sterilized between such uses and without the sterility of such medical devices (260) having to be compromised.

While various configurations for insertion package (200), medical device (260), and cap (290) have been described, various other configurations may be provided as will be apparent to those of ordinary skill in the art in view of the teachings herein. Specifically, it should be understood that while only a single flanged bushing (230) has been described for use with insertion package (200), a plurality of insertion through holes (230) may be provided for use with a plurality of housing openings (272) in medical device (260) for a plurality of insertable components (250), as will be described herein with respect to FIG. 7. Moreover, a plurality of package openings (210) may be provided in a single sidewall (204), multiple sidewalls (204), and/or in base (202). Furthermore, while exemplary insertion package (200) is shown having an integrated package opening (210) and flanged bushing (230), it should be understood that package opening (210), flanged bushing (230) and a portion of sidewall (204) may be made as an independent apparatus separate from insertion package (200), at least partially in accordance with the teachings of sterile insertion window (300) as will be described herein. As yet another merely illustrative variation, threading (232) of flanged bushing (230) may be formed as internal threading, with threading (262) of medical device (260) being formed as external threading.

B. Sterile Insertion Window and Attachment Member

In some settings, a separate and portable apparatus may be desired for protecting a portion of a medical device while inserting a non-sterile component into the device. Some exemplary situations may include when a large or cumbersome medical device must be used and the medical device may not be suitable for use within a package or if insertable components must be switched out quickly either during or between medical operations. Accordingly, an alternative exemplary configuration to insert potentially non-sterile components into a medical device without further contaminating the medical device may include the use of a portable sterile insertion window. An independent sterile insertion window may thus permit more mobile insertion and/or removal of insertable components independent of a container housing the medical device.

Figure 6:
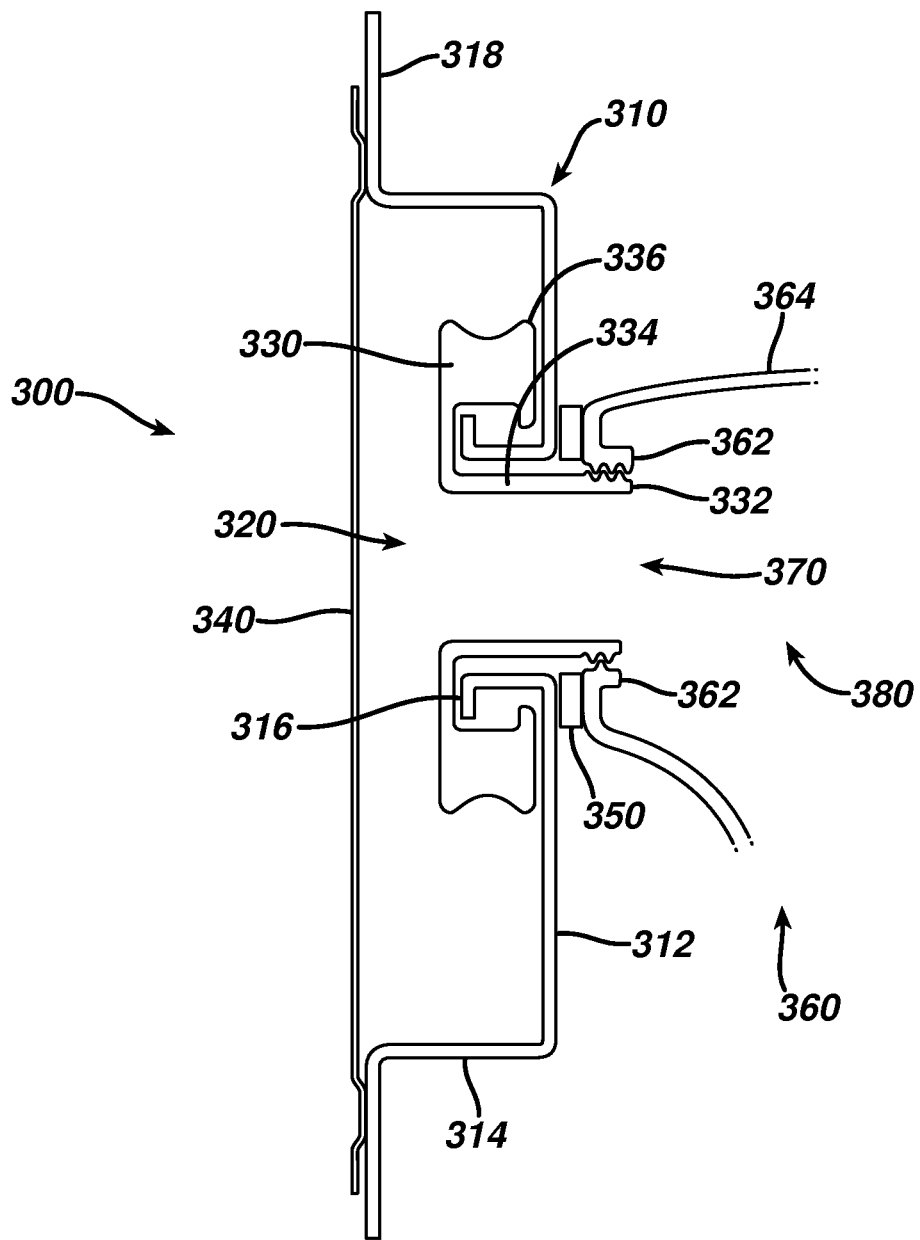
FIG. 6 depicts a partial side cross-sectional view of another exemplary container having a through hole for insertion of a non-sterile internal component into a medical device.

FIG. 6 shows an exemplary sterile insertion window (300) coupled to a medical device (360), which is shown in partial cross-sectional view. Medical device (360) may be constructed in accordance with at least some of the teachings of medical device (10), medical device (100), or medical device (260) as previously described herein; or medical device (360) may have any other suitable configuration as will be apparent to one of ordinary skill in the art in view of the teachings herein. Medical device (360) of the present example comprises a housing (364) defining at least a portion of an interior cavity (380). Interior cavity (380) is sized and configured to receive an insertable component (not shown) that may be constructed at least partially in accordance with insertable component described previously herein. Interior cavity (380) of exemplary medical device (360) is shown as a substantially open cavity within medical device (360); however, it should be understood that interior cavity (380) may be sized to accommodate only the insertable component, a plurality of various insertable components, and/or any other suitable configuration for interior cavity (380) as will be apparent to one of ordinary skill in the art in light of the teachings herein. Housing (364) may be made from a variety of materials including plastics, polyethylene terephthalate glycol (or PETG), thermoplastic polymer resins, or any other suitable rigid material for the housing of medical device (360). Various other materials and configurations for housing (364) may be provided as will be apparent to those of ordinary skill in the art in view of the teachings herein.

Housing (364) further comprises a housing opening (370). Housing opening (370) is sized to permit the passage of the insertable component through housing opening (370) and into interior cavity (380) of medical device (360). Housing opening (370) may be configured at least partially in accordance with housing opening (272) as previously described herein. In the present example, housing opening (370) is a circular opening; however, it should be understood that housing opening (370) may take a variety of geometrical configurations including rectangular, square, triangular, hexagonal, or any other configuration suitable for insertion of insertable component into medical device (360) as will be apparent to one of ordinary skill in the art in light of the teachings herein. Housing opening (370) of the present example is located on a rear surface of medical device (360), though it should be understood that housing opening (370) may be located at a variety of locations of housing (364) including the side, front, bottom, or top surfaces of housing (364) or any other suitable location as will be apparent to those of ordinary skill in the art in light of the teachings herein. Housing (364) of the present example further comprises device threading (362) encircling the perimeter of housing opening (370). Device threading (362) of the present example is configured to complement threading of attachment member (330), as will be described later herein. It should be understood that device threading (362) is merely optional and other attachment configurations may be used to attach medical device (360) to attachment member (330), such as resilient snap-on members, breakaway tabs, or other attachment configurations as will be apparent to one of ordinary skill in the art in view of the teachings herein. Various other configurations for medical device (360), housing opening (370), and/or device threading (362) may be provided as will be apparent to those of ordinary skill in the art in view of the teachings herein.

Exemplary sterile insertion window (300) shown in FIG. 6 comprises a base member (310), an attachment member (330), and a cover (340). Base member (310) comprises a base (312), sidewalls (314), and a rim (318). Base (312), sidewalls (314), and rim (318) of the present example form a homogenous continuum of material and may be made from a variety of materials including plastics, polyethylene terephthalate glycol (or PETG), other thermoplastic polymer resins, or any other suitable rigid or semi-rigid material to maintain sterility as will be apparent to one of ordinary skill in the art in view of the teachings herein. Sidewalls (314) extend distally away from base (312) to form a recess therein. Rim (318) of the present example protrudes outwardly from sidewalls (314). In the present example, base member (310) is a PETG blister tray, but other suitable configurations for base member (310) will be apparent to one of ordinary skill in the art in light of the teachings herein. Cover (340) is attached to rim (318) and is sized and configured to enclose the recess defined by sidewalls (314) and base (312) of base member (310). Cover (340) may be made from a variety of materials including plastics, plastic peelable films, high density polyethylene fiber materials (such as Tyvek® of E. I. du Pont de Nemours and Company of Wilmington, Del.), or any other suitable material to maintain sterility. In the present example, cover (340) is a plastic peelable film adhesively attached to rim (318). Alternatively, cover (340) may be made of a rigid material and attached by mechanical attachment to rim (318), such as by a snap-on lid, screw-on lid, or friction fit lid. Yet another attachment for cover (340) may include heat sealing cover (340) to rim (318). Various other configurations and attachments for cover (340) will be apparent to those of ordinary skill in the art in view of the teachings herein.

Base (312) defines a window opening (320) that is sized and configured to permit passage of an insertable component (not shown) through window opening (320) and housing opening (370) into interior cavity (380) of medical device (360). The insertable component may be configured at least partially in accordance with the teachings for insertable component (250) as previously described herein. Base (312) further comprises a retention feature (316) protruding distally from the surface of base (312) toward cover (340). In the present example, retention feature (316) is a single continuous protrusion from base (312) that encircles window opening (320). However, it should be understood that retention member (316) may alternatively be a plurality of discrete features protruding from base (312) or an independent member coupled to base (312). Retention member (316) of the present example is shown as an L-shaped cross-section revolved about the central axis of window opening (320) to form a circular protrusion having a lip, though it should be understood that this configuration is merely optional. Retention feature (316) may alternatively be a square, rectangular, triangular, or other polygonal protruding feature or any other suitable retention feature (316) as will be apparent to one of ordinary skill in the art in view of the teachings herein.

Attachment member (330) comprises a cylindraceous portion (334), threaded portion (332), and a flange portion (336). In the present example, cylindraceous portion (334) defines an open central channel that is sized to permit passage of an insertable component (not shown) through the opening and into interior cavity (380) of medical device (360). Threaded portion (332) of attachment member (330) is located proximally of through hole portion (334) and is configured to couple with medical device (360). In the present example, threaded portion (332) comprises threading complementing device threading (362). Attachment member (330) may thus be selectively secured to medical device (360) by rotating attachment member (330) relative to base member (310) to selectively engage or disengage threading of threaded portion (332) and threading (362). In some other versions, attachment member (330) may be selectively coupled with medical device (360) by squeezing and releasing retention portion (336) to deform and un-deform threaded portion (332) within threading (362). Of course, any other suitable methods and structures for coupling may be used. Merely exemplary alternative configurations include resilient snap-on attachment members, break-away tabs, or other attachment configurations as will be readily apparent to one of ordinary skill in the art in view of the teachings herein.

In the present example, retention portion (336) extends distally from through hole portion (334) and has a complementary lip to couple with retention feature (316) such that when attachment member (330) is inserted into window opening (320), retention portion (336) and retention feature (316) cooperatively keep attachment member (330) coupled to base member (310) while allowing attachment member (330) to freely rotatae relative to base member (310). Such cooperation may prevent attachment member (330) from being misplaced during a medical procedure. It should also be understood that attachment member (330) may include knurling, recesses, ridges, and/or a variety of other features to facilitate gripping and rotation by a user's hand. Attachment member (330) may be made from a variety of materials including plastics, polyethylene terephthalate glycol (or PETG), other thermoplastic polymer resins, or any other suitable rigid or semi-rigid material. Additionally, various other suitable configurations for attachment member (330) may be provided as will be apparent to one of ordinary skill in the art in view of the teachings herein.

If sterile insertion window (300) is to be transported independently of or decoupled from medical device (360), a second cover (not shown) may be utilized. The second cover may be constructed at least partially in accordance with the teachings of opening cover (220) previously described herein. The second cover may be adhesively attached to the medical device side of base (312) to substantially seal window opening (320) from potential contamination prior to use. While one exemplary implementation of a second cover has been described, various other suitable configurations for the second cover, including implementation of the alternative attachment configurations described in reference to opening cover (220), will be apparent to one of ordinary skill in the art in view of the teachings herein.

Base member (310) may further comprise a seal (350), through it should be understood that this component is merely optional. Seal (350) is sized and configured to encircle window opening (320). Seal (350) in the present example is an o-ring type seal. Seal (350) as shown is attached to the proximal surface of base (312) and abuts housing (364) of medical device (360) when medical device (360) is coupled to sterile insertion window (300). Alternatively, seal (350) may be attached to medical device (360) or seal (350) may be independent of both sterile insertion window (300) and medical device (360). Seal (350) may be made from a variety of materials, including natural rubber, silicone, neoprene, Polytetrafluoroethylene (or PTFE), or other suitable sealing materials as will be apparent to those of ordinary skill in the art in view of the teachings herein. When sterile insertion window (300) of the present example is coupled to medical device (360) by coupling attachment member (330) to device threading (362), seal (350) is compressed to hermetically seal sterile insertion window (300) to medical device (360). Though one exemplary configuration for seal (350) has been described, various other suitable configurations for seal (350) will be apparent to one of ordinary skill in the art in view of the teachings herein.

In some settings, sterile insertion window (300) may be used in a manner similar to the use of package (200) as described above, though it is contemplated that insertion window (300) may be used more than once and with more than one medical device (360). In one merely exemplary use, initially the second cover (not shown), if provided, is detached from base (312) and threaded portion (332) of attachment member (330) is coupled to medical device (360). In the present example, threading of threaded portion (332) is threaded into complementary device threading (362) of medical device (360), as shown in FIG. 6, and attachment member (330) is rotated to tighten attachment member (330) to medical device (360). If seal (350) is provided, seal (350) is compressed between base (312) and housing (364) of medical device (360) to form a hermetic seal. This may further prevent contamination of the exterior of medical device (360) when a non-sterile insertable component is inserted into medical device (360) through the channel of attachment member (330). Once medical device (360) is coupled to attachment member (330), cover (340) may be detached to expose window opening (320) to access interior cavity (380) of medical device (360). In the present example, cover (340) is a plastic peelable film that is peeled off from rim (318) of base member (310). With cover (340) removed, an insertable component (not shown) is then inserted through the channel of attachment member (330) and into interior cavity (380) of medical device (360). Thus, even with parts of medical device (360) exposed to the environment, insertion window (300) protects the exterior of medical device (360) from being inadvertently contaminated by an insertable component as the insertable component is being inserted into medical device (360). In other words, window (300) serves as a sterile barrier between the insertable component and the exterior of medical device (360).

Once the insertable component has been inserted into medical device (360), medical device (360) is detached from attachment member (330). In the present example, attachment member (330) is unscrewed from medical device (360). Alternatively, medical device (360) may be unscrewed from threaded portion (332) of attachment member (330); or retention portion (336) of attachment member (330) may be squeezed to deform threaded portion (332) inwardly and away from device threads (362), thereby releasing medical device (360). Once detached, medical device (360) may then be used or further assembled. One such further assembly may include coupling a cap, such as one constructed at least partially in accordance with the teachings of cap (290) described herein, to medical device (360) to seal interior cavity (380) of medical device (360). Sterile insertion window (300) may then be properly disposed, kept for later removal of the insertable component from the dirty medical device (360), or resterilized and resealed for use with a different medical device (360).

Once medical device (360) has been used (or if the insertable component needs to be recharged or replaced during a medical procedure, etc.), the same insertion window (300) or a new, sterile insertion window (300) may be coupled with medical device (360) in the manner described above. The insertable component may then be removed through openings (320, 370). Again, in this instance insertion window (300) may serve as a barrier to prevent the used insertable component from further contaminating medical device (360) as the insertable component is removed from medical device (360).

In addition or in the alternative (e.g., when medical device (360) is covered in bodily fluids, etc.), insertion window (300) may act as a barrier to prevent the used insertable component from being further contaminated by medical device (360) as the insertable component is removed from medical device (360). Once removed from medical device (360), the insertable component may be processed as described elsewhere herein and/or in any other suitable fashion. To the extent that the same insertable component or another insertable component needs to again be inserted into medical device (360), the same insertion window (300) or yet another new, sterile insertion window (300) may be coupled with medical device (360) in the manner described above to start the insertion process all over again.

While the exemplary sterile insertion window (300) shown in FIG. 6 is depicted as an independent apparatus, it should be understood this is merely optional. As will be apparent to one of ordinary skill in the art in light of the teachings herein, exemplary sterile insertion window (300) may be readily incorporated, in part or in whole, into insertion package (200) of FIGS. 4-5. Sterile insertion window (300) may be implemented instead of flanged bushing (230) and/or as a separate insertion option for insertion package (200). Additionally, various other suitable configurations and uses for sterile insertion window (300) will be readily apparent to one of ordinary skill in the art in view of the teachings herein.

C. Insertion Package for Use with Multiple Insertable Components

Figure 7:
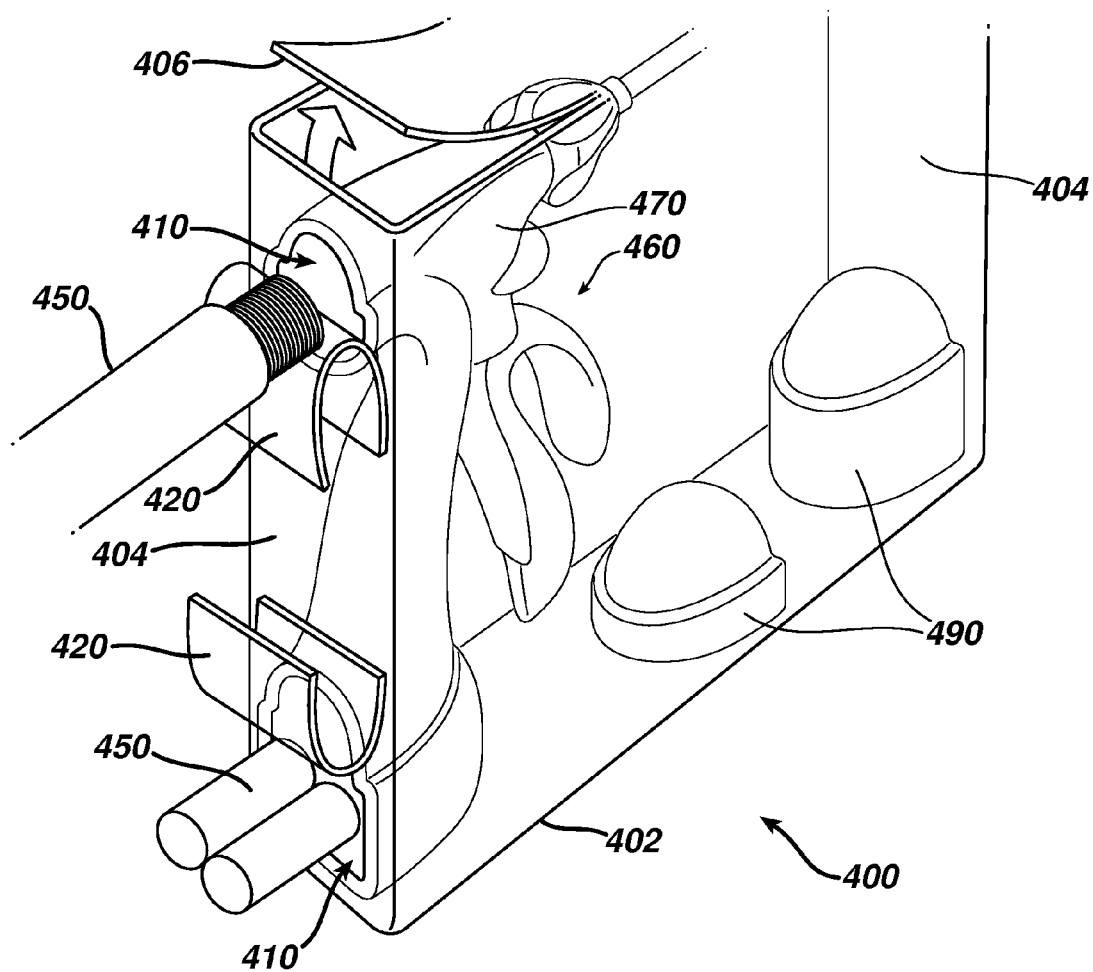
FIG. 7 depicts a perspective view of yet another exemplary package having multiple insertion through holes for non-sterile internal components.

FIG. 7 depicts an exemplary alternative insertion package (400) for inserting a plurality of insertable components (450) into a medical device (460) without compromising the sterility of the medical device (460). By way of example only, the plurality of insertable components (450) may include power sources, such as the types of batteries previously discussed herein, pluralities of batteries in the forms of battery packs, printed circuit boards, control modules, ultrasonic transducers (e.g., un ultrasonic transducer pack that needs to be torque onto an acoustic wave guide, etc.), blades, end effectors, and/or any other insertable components or combination of components as will be apparent to those of ordinary skill in the art in view of the teachings herein. Exemplary medical device (460) may be constructed in accordance with at least some of the teachings of medical devices (10), (100), (260), or (360) as previously described herein or medical device (460) may have any other suitable configuration as will be apparent to one of ordinary skill in the art in view of the teachings herein. Exemplary medical device (460) comprises a housing (470). Housing (470) of the present example at least partially defines an interior cavity (not shown) configured to receive insertable component (450) or a plurality of insertable components (450). In the present example, housing (470) is shown with two openings configured to permit passage of insertable components (450) into the respective interior cavities of medical device (460). While one exemplary configuration of medical device (460) has been described, other suitable configurations for medical device (460) may be provided as will be apparent to one of ordinary skill in the art in view of the teachings herein.

Insertion package (400) of the present example comprises a base (402), sidewalls (404), and a cover (406). In the present example, base (402) and sidewalls (404) form a homogeneous continuum of material and may be made from a variety of materials including plastics, polyethylene terephthalate glycol (or PETG), other thermoplastic polymer resins, or any other suitable rigid or semi-rigid material to maintain sterility. Cover (406) may also be made from a variety of materials including plastics, plastic peelable films, high density polyethylene fiber materials (such as Tyvek® of E. I. du Pont de Nemours and Company of Wilmington, Del.), or any other suitable material to maintain sterility. In the present example, cover (406) is adhesively attached to sidewalls (404) to seal insertion package (400). Cover (406) may alternatively be attached by mechanical attachments such as a snap-on lid, screw-on lid, or friction fit lid. Yet another method for attaching cover (406) may include heat sealing cover (406) to sidewalls (404). In the present example, insertion package (400) is a rectangular package having a substantially open interior. In one alternative, insertion package (400) may be configured as a blister tray comprising a form-fitting recess for medical device (460) such that, when medical device (460) is inserted into the blister tray, the openings in housing (470) of medical device (460) align with the package openings (410), as will be described. Various other configurations of insertion package (400) and attachment methods for attaching cover (406) to insertion package (400) may be provided as will be apparent to those of ordinary skill in the art in view of the teachings herein.

Insertion package (400) further comprises a plurality of package openings (410). In the present example, two package openings (410) are shown formed in sidewall (404), though it should be understood that the plurality of package openings (410) may alternatively be formed in base (402), sidewalls (404), and/or cover (406) of insertion package (400) or any combination thereof. Package openings (410) are sized and configured to permit the passage of insertable components (450) through each respective package opening (410) and into the respective interior cavities of medical device (460). In the present example, each package opening (410) is sized and configured to correspond to the insertion of a different insertable component (450). As shown, the top package opening (410) is sized for insertion of an ultrasonic transducer component while the bottom package opening (410) is sized for insertion of a battery pack component. It should be understood that package openings (410) may take a variety of geometrical configurations including rectangular, square, triangular, hexagonal, or any other configuration suitable for insertion of a corresponding insertable component (450) as will be apparent to one of ordinary skill in the art in light of the teachings herein. Moreover, more than two package openings (410) may be provided for inserting any number of insertable components (450) into medical device (460) as will be apparent to one of ordinary skill in the art in view of the teachings herein.

Insertion package (400) may further include insertion through holes (not shown) or attachment members (not shown) within package openings (410) constructed in accordance with at least some of the teachings of flanged bushing (230) and/or attachment member (330) as previously described herein and/or any other suitable components, features, or configuration as will be apparent to one of ordinary skill in the art in view of the teachings herein.

Insertion package (400) of the present example further comprises a plurality of opening covers (420). Opening covers (420) may be constructed at least partially in accordance with the teachings of opening covers (220) as previously described herein. Opening covers (420) may be made from a variety of materials including plastics, plastic peelable films, high density polyethylene fiber materials (such as Tyvek®), or any other suitable material to maintain sterility. Opening covers (420) are sized and configured to seal a corresponding package opening (410) of insertion package (400) prior to use. In the present example, opening covers (420) are attached by an adhesive, such as cyanoacrylate or epoxy, to sidewall (404) of insertion package (400). Alternatively, opening covers (420) may be configured to mechanically attach to sidewall (404), such as by snapping-on to a rim (not shown) protruding from sidewall (404). A further exemplary mechanical attachment may include threading opening covers (420) onto the protruding rim. In yet a further exemplary configuration, opening covers (420) may be heat sealed to sidewall (404) of insertion package (400) to seal package openings (410). If insertion through holes are utilized, opening covers (420) may be adhesively attached, mechanically attached, or heat sealed to the insertion through holes instead of attaching opening covers (420) to sidewall (404). Opening covers (420) are configured to provide a sterile barrier across openings (410), maintaining the sterility of the interior of package (400) when covers (420) are in a closed position. Various other materials and other suitable configurations for opening covers (420) may be provided as will be apparent to those of ordinary skill in the art in view of the teachings herein.

In the present example, caps (490) are included within insertion package (400) for sealing insertable components (450) within medical device (460). Caps (490) may be constructed in accordance with at least some of the teachings of cap (290) (e.g., screwed onto medical device (460)), as previously described herein, or caps (490) may have any other suitable configuration (e.g., snapped onto medical device (460), etc.) as will be apparent to one of ordinary skill in the art in view of the teachings herein.

For the initial assembly of insertion package (400), medical device (460) is inserted into insertion package (400) and the plurality of device openings on medical device (460) are aligned with the plurality of package openings (410). If insertion through holes and/or attachment members are provided, medical device (460) may be coupled to the insertion through holes or attachment members, though it should be understood that this is merely optional. Caps (490) are also placed within and/or secured to insertion package (400). In some versions, caps (490) may be secured to medical device (460) through a hinged connection, for example, prior to insertion of the insertion package (400). In the present example, cover (406) is attached to sidewalls (404) to seal medical device (460) and caps (490) within insertion package (400). Opening covers (420) are then attached to sidewall (404) to seal package openings (410). As previously discussed herein, opening covers (420) may be adhesively attached to sidewall (404) or, alternatively, opening covers (420) may be mechanically attached to sidewall (404) as will be apparent to those of skill in art in light of the teachings herein. Once medical device (460) and caps (490) are contained within insertion package (400) and cover (406) and opening covers (420) are attached, insertion package (400) is in a ready-to-use state. Other various suitable arrangements and assemblies of insertion package (400) will be apparent to those of ordinary skill in the art in view of the teachings herein.

Insertion package (400), including medical device (460) and caps (490), is then sterilized. In one exemplary sterilization technique, insertion package (400) is placed in a field of radiation that can penetrate insertion package (400), such as gamma radiation, x-rays, or high-energy electrons. The radiation may kill bacteria on medical device (460), caps (490), and within insertion package (400). Insertion package (400), medical device (460), and caps (490) may also be sterilized using any other technique known in the art, including but not limited to beta or gamma radiation, ethylene oxide, electron beam sterilization, or steam. The sterilized insertion package (400) containing medical device (460) and caps (490) may then be stored or shipped to a medical facility for use. Of course, one or more components of medical device (460) and caps (490) may be sterilized before being sealed within insertion package (400), if desired (e.g., in instances where different components warrant different sterilization techniques, etc.).

Once a user wants to utilize medical device (460), the user initially detaches opening covers (420) to expose the interior cavities of medical device (460) to insert insertable components (450) therein. Insertable components (450) may be sterilized or non-sterilized when they are inserted into medical device (460). It should be understood that insertion of insertable components (450) through package openings (410) may permit the use of non-sterilized insertable components (450) to be used and/or reused within medical device (460) by reducing or eliminating the risk of contamination to the sterilized exterior of medical device (460). Opening covers (420) may then be resealed, though it should be understood this is merely optional.

Following the insertion of insertable components (450) into medical device (460), cover (406) is detached to expose medical device (460) within insertion package (400). Medical device (460) of the present example is then removed from insertion package (400). If insertion through holes and/or attachment members are used with medical device (460) and insertion package (400), such as flanged bushing (230) or attachment member (330) as described herein, the appropriate decoupling or detachment may be done to remove medical device (460). Once medical device (460) is detached, caps (490) are attached to medical device (460) to close and seal insertable components (450) within each respective interior cavity of medical device (460). Medical device (460) may then be used to perform a medical operation.

While various configurations for insertion package (400), medical device (460), and caps (490) have been described, various other configurations may be provided as will be apparent to those of ordinary skill in the art in view of the teachings herein.

Once a medical device, such as one constructed in accordance with at least some of the teachings of medical devices (10), (100), (260), (360), or (460) as described herein, has been used in a procedure, the used medical device may be returned to an insertion package, such as insertion packages (200) or (400) as described herein, or coupled to a sterile insertion window, such as sterile insertion window (300) as described herein, to remove the insertable component or insertable components from within the used medical device. By way of example only, for the system described in reference to insertion package (400) of FIG. 7, caps (490) may be detached from used medical device (460) and either returned to insertion package (400) or properly disposed of elsewhere. Used medical device (460) having a plurality of openings in housing (470) with insertable components (450) contained therein is then reinserted into insertion package (400) and the device openings are aligned with package openings (410). If attachments are used with medical device (460) and insertion package (400), such as flanged bushing (230) of FIGS. 4-5 or attachment member (330) of FIG. 6 as described herein, those attachments may be reattached to used medical device (460) to secure used medical device (460) within insertion package (400). Once used medical device (460) is reattached, opening covers (420) may be detached from sidewall (404) to re-expose package openings (410) and insertable components (450) contained within used medical device (460). The user may then remove the insertable components (450) through package openings (410). This may permit a user to avoid potential contamination of the insertable components (450) from the exterior of the used medical device (460). With the insertable components (450) removed, opening covers (420)

and cover (406) may be re-attached to sidewalls (404) with the used medical device (460) and caps (490) contained therein. Insertion package (400) with used medical device (460) and caps (490) may then be disposed or returned for reclamation.

Having removed insertable components (450), a user may then test, store, and/or recharge the various components at a testing, recharging, and/or storage station. If insertable components (450) have been incidentally contaminated, insertable components (450) may be cleaned and/or resterilized prior to recharging, storage, and/or testing. Once insertable components (450) are ready for use again, insertable components (450) may be inserted into a new medical device (460) utilizing a new insertion package (400). Insertable components (450) may be inserted into a new medical device (460) for pre-testing medical device (460) to ensure medical device (460) and insertable components (450) work properly prior to use.

While the above-described reuse of exemplary insertable components (450) has been described in reference to exemplary insertion package (400), it should be understood that the foregoing may be equally applicable for use with insertion package (200) of FIGS. 4-5, sterile insertion window (300) of FIG. 6, and/or any combination of the packages and/or windows herein described, or any other combination incorporating at least some of the features of the packages or windows herein described as will be apparent to one of ordinary skill in the art in view of the teachings herein. Additionally, various other suitable configurations and reconditioning processes for testing, storing, and/or recharging insertable components (450) will be apparent to one of ordinary skill in the art in view of the teachings herein.

III. Alternative Exemplary Packaging Utilizing Multiple Packages to Insert a Non-Sterile Component into a Medical Device In some instances, it may be advantageous to provide separate packages for multiple portions of the medical device. One exemplary instance might be if one portion of the medical device has sensitive electronic components while the other portion does not. This may permit alternative sterilization techniques for each packaged portion. This may also facilitate insertion of a non-sterile component into a sterile medical device without compromising the sterility of the medical device. Accordingly, the following examples relate to various illustrative ways in which separately packaged medical device components may be coupled together while maintaining the sterility of the exterior of the medical device.

Figure 8A:
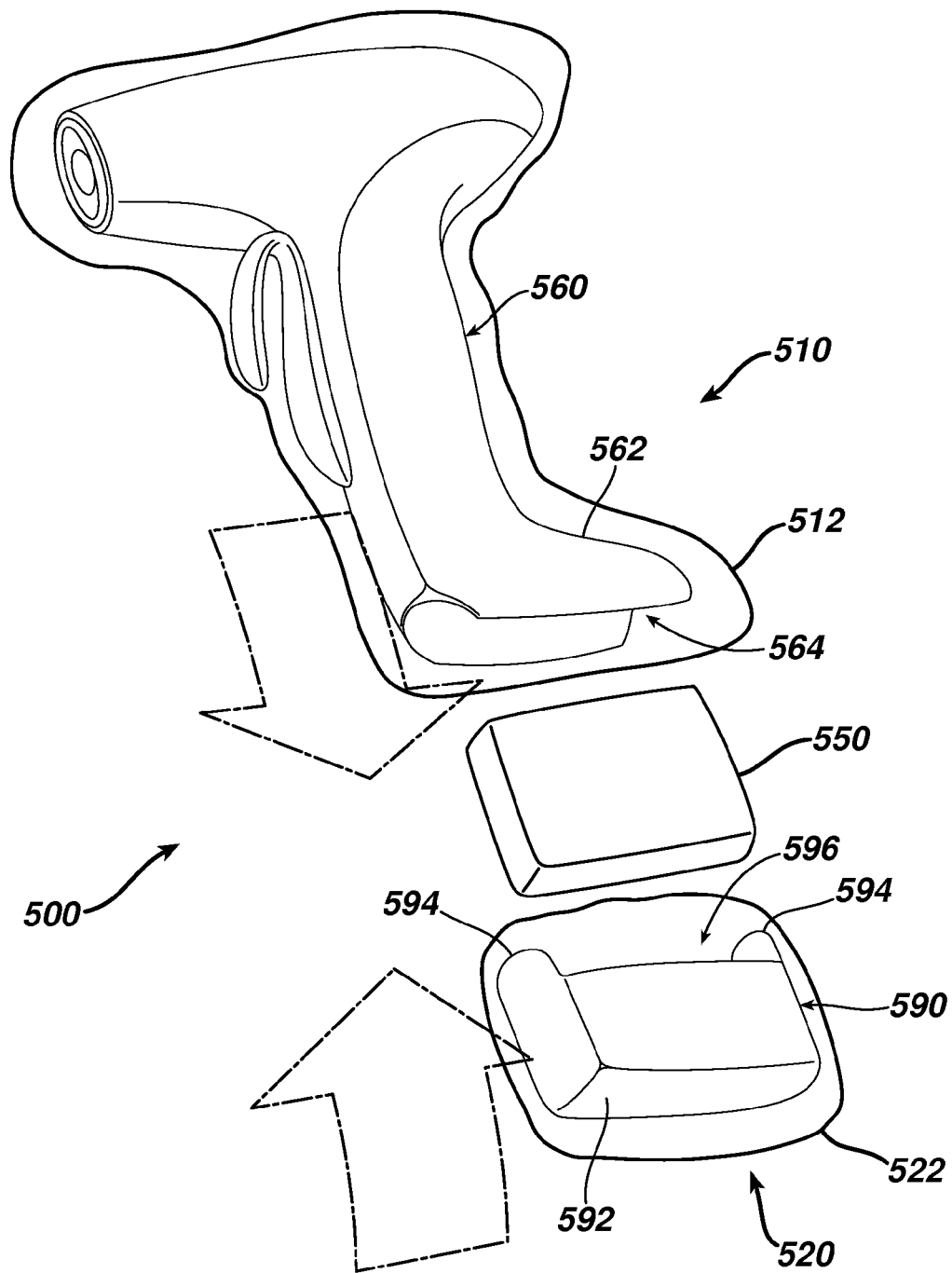
FIG. 8A depicts a perspective view of an exemplary package system for inserting a non-sterile internal component into a medical device.
Figure 8B:
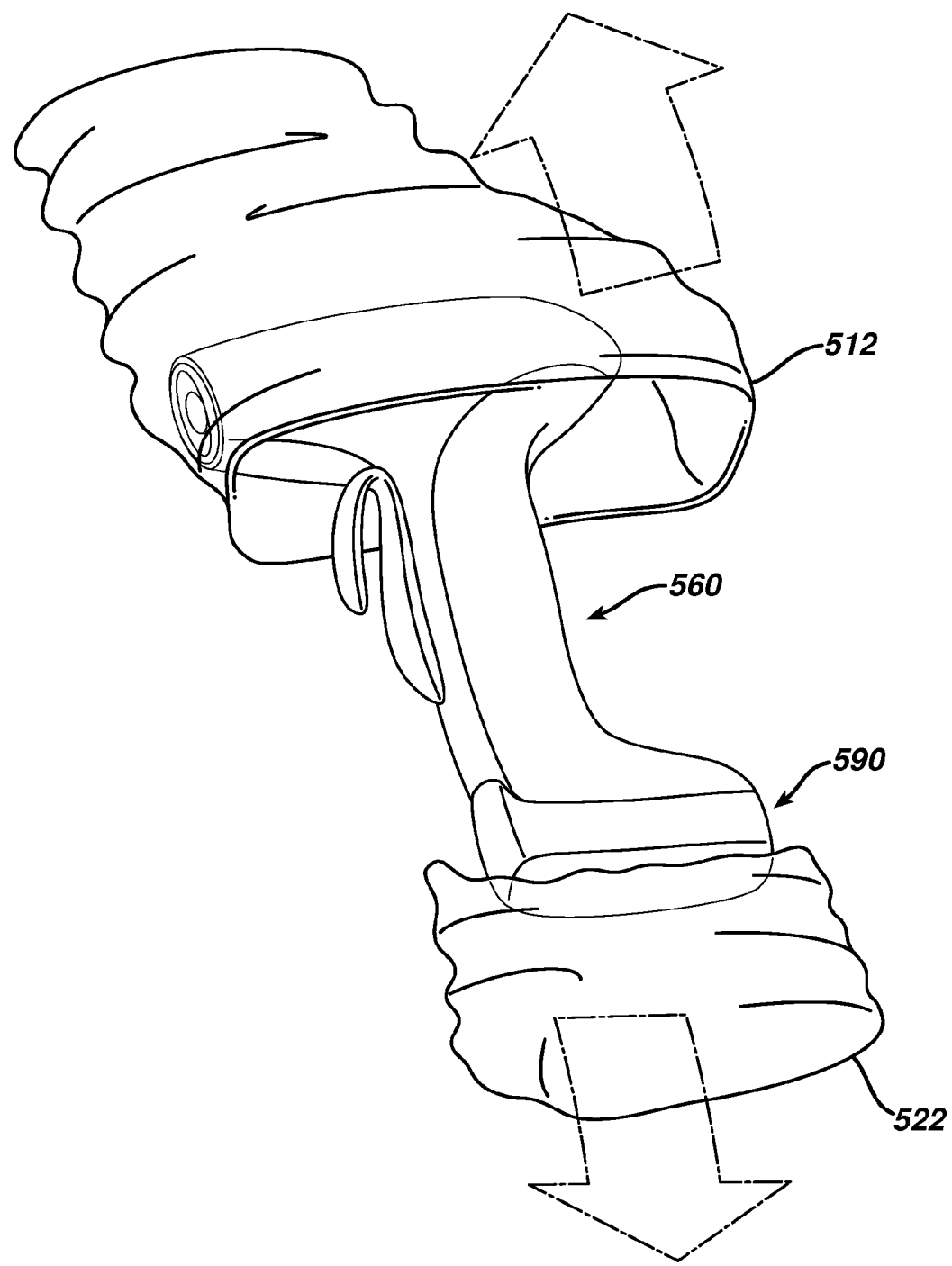
FIG. 8B depicts a perspective view of the exemplary package system of FIG. 8A, showing the non-sterile internal component inserted into the medical device.

Referring to FIGS. 8A-8B, an alternative sterile packaging system (500) is shown for inserting an insertable component (550) (sterile or non-sterile) into a medical device (560) for use without contaminating the exterior of medical device (560). Medical device (560) of the present example comprises a housing (562) and an insertion recess (564) at least partially defined by a portion of housing (562). Medical device (560) may further be constructed in accordance with at least some of the teachings of medical devices (10), (100), (260), (360), or (460) as previously described herein or medical device (560) may have any other suitable configuration as will apparent to one of ordinary skill in the art in view of the teachings herein. By way of example only, insertable component (550) may comprise a power source, such as one of the types of batteries previously discussed herein, a plurality of batteries in the form of a battery pack, a printed circuit board, a control module, an ultrasonic transducer, and/or any other insertable component or combination of components as will be apparent to those of ordinary skill in the art in view of the teachings herein.

Sterile packaging system (500) comprises a first package (510) and a second package (520). First package (510) comprises a first package material (512) configured to contain medical device (560) therein. In the present example, first package material (512) comprises a thin flexible material, such as polyethylene or any other suitable flexible material. Alternatively, first package material (512) may comprise a rigid or semi-rigid portion and a flexible portion, wherein the flexible portion substantially surrounds or covers insertion recess (564) of medical device (560) while the rigid or semi-rigid portion encases the other portions of medical device (560), as will be discussed in more detail in reference to FIGS. 9A-9C. In another alternative, first package material (512) may substantially conform to the profile of medical device (560), such as in the case of a heat-shrunk plastic material or by vacuuming out the air within first package (510) prior to sealing. Various other suitable configurations for first package (510) will be apparent to one of ordinary skill in the art in view of the teachings herein.

Second package (520) comprises a second package material (522) configured to contain an attachable member (590) therein. In the present example, attachable member (590) is a cap comprising a cap housing (592) and attachment protrusions (594) configured to couple to medical device (560) and encase insertion recess (564). However, it should be understood that attachable member (590) may include any member that may be coupled to a medical device, including, but not limited to, an end effector, a portion of a medical device housing, a cap containing electronic components, or any other suitable attachable member (590) as will be apparent to one of ordinary skill in the art in view of the teachings herein. In reference to the present example, cap housing (592) is sized and configured to at least partially contain a portion of insertable component (550) within a cap recess (596) defined at least in part by cap housing (592). Attachment protrusions (594) extend proximally from cap housing (592) and are configured to couple with housing (562) of medical device (560). In the present example, attachment protrusions (594) comprise snap-on connectors, though it should be understood a variety of other coupling configurations may be used.

In the present example, second package material (522) comprises a thin flexible material, such as polyethylene or any other suitable flexible material. Alternatively, second package material (522) may comprise a rigid or semi-rigid portion and a flexible portion, wherein the flexible portion substantially surrounds or covers cap recess (596) of attachable member (590) while the rigid or semi-rigid portion encases the rest of attachable member (590), as will be discussed in more detail in reference to FIGS. 9A-9C. In another alternative, second package material (522) may substantially conform to the profile of attachable member (590), such as in the case of a heat-shrunk material or by vacuuming out the air within second package (520) prior to sealing. Various other suitable configurations for attachable member (590) and second package material (522) will be apparent to one of ordinary skill in the art in view of the teachings herein.

Prior to use, medical device (560) is inserted into first package material (512) and first package material (512) is sealed. In one exemplary method, first package material (512) is sealed by heating and sealing the open portion of first package material (512) to seal medical device (560) therein. Alternatively, first package material (512) may be adhesively sealed or otherwise be sealed. Once first package (510) is constructed, first package (510) is then sterilized. In one exemplary sterilization technique, first package (510) is placed in a field of radiation that can penetrate first package (510), such as gamma radiation, x-rays, or high-energy electrons. The radiation may kill bacteria on medical device (560) and within first package (510). First package (510) may alternatively be sterilized using any other technique known in the art, including but not limited to beta or gamma radiation, ethylene oxide, electron beam sterilization, or steam. The sterilized first package (510) may then be stored or shipped to a medical facility for use. Of course, medical device (560) may be sterilized before being packaged within first package (510), if desired.

Attachable member (590) is also inserted into second package material (522) and second package material (522) is sealed. In one exemplary method, second package material (522) is sealed by heating and sealing the open portion of second package material (522) to seal attachable member (590) therein. Alternatively, second package material (522) may be adhesively sealed. Once second package (520) is constructed, second package (520) is then sterilized. Second package (520) is placed in a field of radiation that can penetrate second package (520), such as gamma radiation, x-rays, or high-energy electrons. The radiation may kill bacteria on attachable member (590) and within second package (520). Second package (520) may alternatively be sterilized using any other technique known in the art, including but not limited to beta or gamma radiation, ethylene oxide, electron beam sterilization, or steam. The sterilized second package (520) may then be stored or shipped to a medical facility for use. Again, attachable member (590) may be sterilized before being packaged within second package (520), if desired.

When a user requires the use of medical device (560), first package (510) containing medical device (560), insertable component (550), and second package (520) containing attachable member (590) are aligned for insertion and coupling, as shown in FIG. 8A. The user then pushes medical device (560) and attachable member (590) together by holding first package material (512) and second package material (522). Attachment protrusions (594) of attachable member (590) couple to housing (562) through the flexible material of first package material (512) and second package material (522). Thus, insertable component (550) is encased within insertion recess (564) and cap recess (596) while limiting if not eliminating the risk of contamination from non-sterile insertable component (550). Once attachable member (590) and medical device (560) are coupled, the user then opens first package material (512) and second package material (522), as shown in FIG. 8B, to expose the assembled medical device (560) with attachable member (590) coupled thereto. In the present example, the user may simply tear open first package material (512) and second package material (522).

In some versions, when a user tears open first package material (512) and second package material (522), this will result in package material (512, 522) that is captured between medical device (560) and attachable member (590) being pulled free. This may enable any contacts, terminals, etc. within medical device (560) and/or attachable member (590) to communicate electrically/electronically with corresponding features of insertable component (550), without package material (512, 522) providing a barrier to such communication. In addition or in the alternative, insertable component (550), medical device (560), and/or attachable member (590) may include one or more internal features (e.g., spikes, etc.) configured to pierce package material (512, 522) that is captured between medical device (560) and attachable member (590). Various other suitable ways in which insertable component (550), medical device (560), and/or attachable member (590) may be configured to prevent package material (512, 522) from inhibiting electrical/electronic communication between insertable component (550) and medical device (560) and/or attachable member (590) will be apparent to those of ordinary skill in the art in view of the teachings herein. With insertable component (550) contained in medical device (560) and with the necessary electrical/electronic communication being provided, medical device (560) can then be used by a user for a procedure. Various other suitable configurations for inserting insertable component (550) into medical device (560) utilizing sterile packaging system (500) will be apparent to one of ordinary skill in the art in view of the teachings herein.

FIGS. 9A-9C and 10 depict an exemplary alternative sterile package system (600) comprising a first package (610) and a second package (670). First package (610) is sized and configured to contain an insertable component (650) therein. By way of example only, the insertable component (650) may comprise a power source, such as one of the types of batteries previously discussed herein, a plurality of batteries in the form of a battery pack, a printed circuit board, a control module, an ultrasonic transducer, and/or any other insertable component or combination of components as will be apparent to those of ordinary skill in the art in view of the teachings herein.

First package (610) of the present example comprises a base (612), sidewalls (614), a rim (616), and a cover (620). Base (612) and sidewalls (614) of first package (610) define a recess sized to contain insertable component (650) therein. Base (612) and sidewalls (614) may be made from a variety of materials including plastics, polyethylene terephthalate glycol (or PETG), other thermoplastic polymer resins, or any other suitable semi-rigid material. By way of example only, sidewalls (614) of the present example are configured with accordion-like folds such that when a user applies a force to base (612), the accordion-like folds compress to reduce the distance between rim (616) and base (612) of first package (610). Sidewalls (614) may be configured in a variety of other manners to be compressed as will be apparent to one of ordinary skill in the art in light of the teachings herein. Rim (616) extends substantially perpendicular from the top of sidewalls (614) to form a substantially flat top surface for first package (610). Rim (616) comprises at least one recess (618). By way of example only, exemplary first package (610) comprises four recesses (618) at the four corners of rim (616). Recesses (618) are configured to couple to protrusions (682) from second package (670), as will be later described herein. One exemplary configuration to couple recess (618) to protrusion (682) is by a friction fit attachment.

Figure 9A:
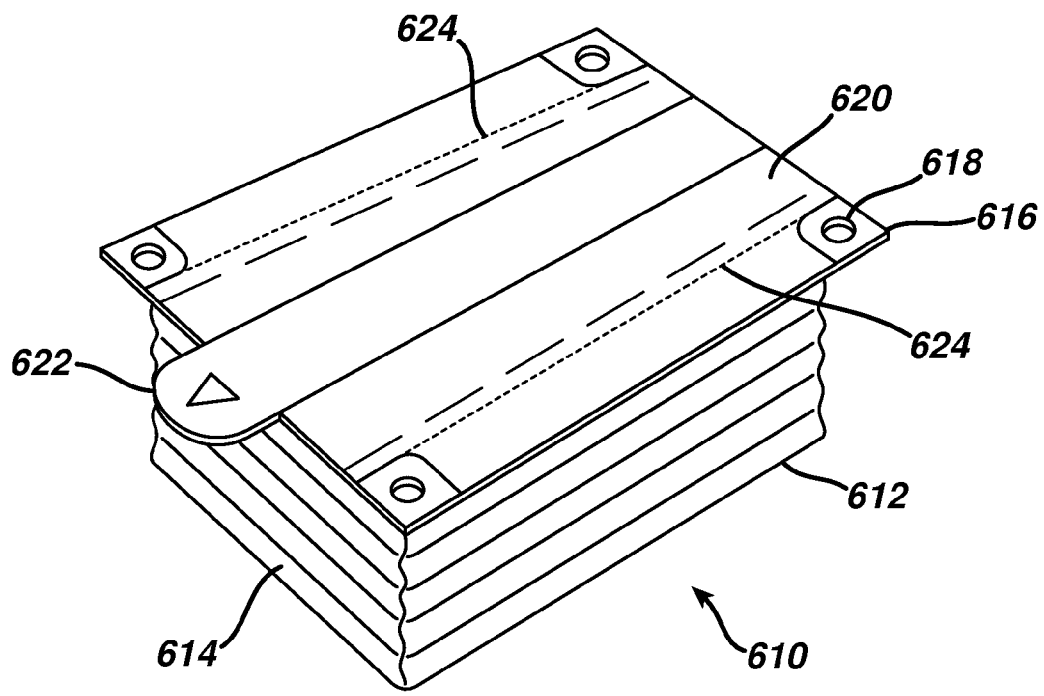
FIG. 9A depicts a perspective view of an exemplary non-sterile internal component package for use in a package system.

First package (610) further comprises a first cover (620) detachably attached to rim (616). First cover (620) may be made from a variety of materials including plastics, plastic peelable films, high density polyethylene fiber materials (such as Tyvek® of E. I. du Pont de Nemours and Company of Wilmington, Del.), or any other suitable flexible material to maintain sterility. First cover (620) in the present example is adhesively attached to rim (616) to seal first package (610) when insertable component (650) is contained therein. First cover (620) may alternatively be attached by mechanical attachment to rim (616), such as a snap-on lid, screw-on lid, or friction fit lid. Yet another method of attachment for first cover (620) may comprise heat sealing first cover (620) to rim (616). First cover (620) of the present example further comprises a pull tab (622). Exemplary pull tab (622) is integrally formed with first cover (620) and is configured such that when pull tab (622) is pulled substantially parallel to the surface of first cover (620), first cover (620) detaches from rim (618) to expose insertable component (650) contained within first package (610). One exemplary configuration for pull tab (622) is for pull tab (622) to be integrally attached to first cover (620) at a first end of first cover (620) and to extend along the span of first cover (620) and beyond a second end of first cover (620), as shown in FIG. 9A. In the current example, first cover (620) further comprises a plurality of perforations (624) provided between an interior edge of rim (616) and recesses (618) such that when pull tab (622) is pulled, perforations (624) detach and a majority of first cover (620) is separated from a lesser portion that remains attached to rim (616). While various configurations of first cover (620) have been described, other various configurations and attachment methods for detachably attaching first cover (620) to rim (616) may be provided as will be apparent to those of ordinary skill in the art in view of the teachings herein.

Figure 9B:
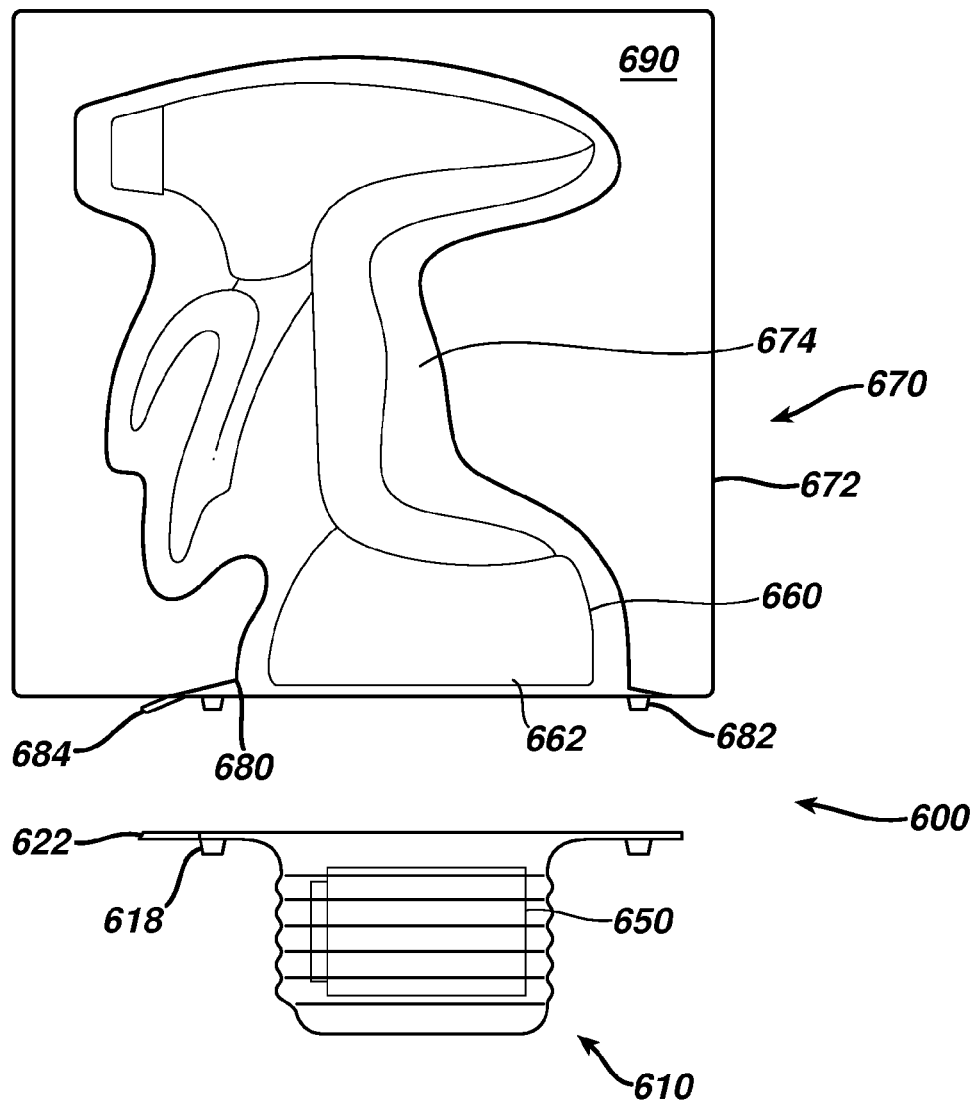
FIG. 9B depicts a side view of the exemplary internal component package of FIG. 9A showing the internal component package in position for attachment to an exemplary medical device package.

Referring to FIG. 9B, exemplary sterile package system (600) includes second package (670). Second package (670) is sized and configured to contain a medical device (660) therein. Medical device (660) may be constructed in accordance with at least some of the teachings of medical devices (10), (100), (260), (360), (460), or (560) as previously described herein or medical device (660) may have any other suitable configuration as will be apparent to one of ordinary skill in the art in view of the teachings herein. In the present example, medical device (660) comprises a bottom portion (662) having a cavity (not shown) sized and configured to receive insertable component (650) therein. Second package (670) comprises a container (672), a main cover (690), and a second cover (680). Container (672) is a semi-rigid or rigid container having a recess (674) sized and configured to receive medical device (660). Container (672) may be made from a variety of materials such as plastics, polyethylene terephthalate glycol (or PETG), other thermoplastic polymer resins, or any other suitable rigid or semi-rigid material. In the present example, container (672) comprises a blister tray. In an alternative configuration, container (672) may be a substantially open container, such as a rectangular, square, or other polygonal container.

Primary cover (690) is detachably attached to container (672) to enclose medical device (660) therein. Primary cover (690) may be made from a variety of materials including plastics, plastic peelable films, high density polyethylene fiber materials (such as Tyvek®), biaxially-oriented polyethylene terephthalate (BoPET, such as Mylar® of E. I. du Pont de Nemours and Company of Wilmington, Del.), or any other suitable material to maintain sterility. In the present example, primary cover (690) is adhesively attached to container (672). Exemplary adhesives include cyanoacrylate, epoxy, or other epoxy resins. Alternatively, primary cover (690) may be configured to mechanically attach to container (672), such as a snap-on cover, screw-on cover, or friction fit cover. In yet a further exemplary configuration, primary cover (690) may be heat sealed to container (672) to seal second package (670). Various other materials for primary cover (690) and other suitable methods to attach primary cover (690) to container (672) will be apparent to those of ordinary skill in the art in view of the teachings herein.

Figure 10:
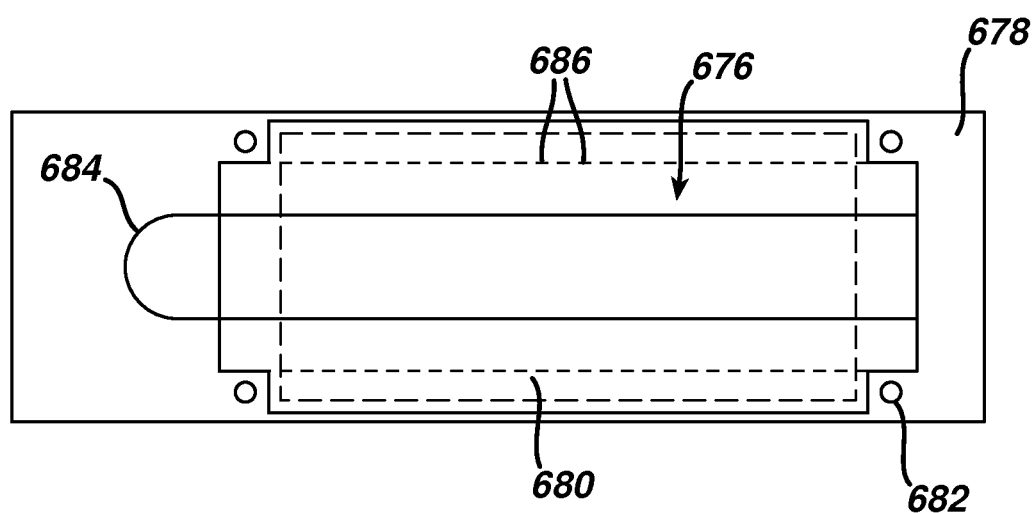
FIG. 10 depicts a bottom view of the exemplary medical device package of FIG. 9B.

Referring to FIG. 10, container (672) further comprises a bottom surface (678). An opening (676) is formed in recess (674) at bottom surface (678). Opening (676) is located to substantially correspond to the area of bottom portion (662) of medical device (660) such that insertable component (650) may be inserted into medical device (660) through opening (676). Bottom surface (678) further comprises a plurality of protrusions (682). Protrusions (682) extend away from bottom surface (678) and are configured to couple with recesses (618) shown in FIG. 9A. Exemplary second package (670) comprises four protrusions (682) corresponding to the four recesses (618) of first package (610). In the present example, protrusions (682) are a cylindrical protrusions configured to frictionally fit and couple to recesses (618).

Second package (670) also comprises a second cover (680) detachably attached to bottom surface (678) of container (672). Second cover (680) may be made from a variety of materials including plastics, plastic peelable films, high density polyethylene fiber materials (such as Tyvek® of E. I. du Pont de Nemours and Company of Wilmington, Del.), biaxially-oriented polyethylene terephthalate (BoPET, such as Mylar® of E. I. du Pont de Nemours and Company of Wilmington, Del.), or any other suitable flexible material to maintain sterility. Second cover (680) is sized and configured to cover and seal opening (676). In the present example, second cover is adhesively attached to bottom surface (678). Second cover (680) may alternatively be attached by mechanical attachment such as a snap-on lid, screw-on lid, or friction fit lid to bottom surface (678). Yet another exemplary method of attachment for second cover (680) may include heat sealing second cover (680) to bottom surface (678).

Second cover (680) of the present example further comprises a pull tab (684). Exemplary pull tab (684) is integrally formed with second cover (680) and is configured such that when pull tab (684) is pulled substantially parallel to the surface of second cover (680), second cover (680) detaches from bottom surface (678) to expose opening (676) in recess (674). One exemplary configuration for pull tab (684) is for pull tab (684) to be integrally attached to second cover (680) at a first end of second cover (680) and to extend along the span of second cover (680) and beyond a second end of second cover (680), as shown in FIG. 10. In the present example, second cover (680) further comprises a plurality of perforations (686). Perforations (686) are configured such that when pull tab (684) is pulled, perforations (686) detach and a majority of second cover (680) is separated from a lesser portion that remains attached to a portion of bottom surface (678). While certain configurations of second cover (680) have been described, other suitable configurations and attachment methods for detachably attaching second cover (680) to bottom surface (678) may be provided as will be apparent to those of ordinary skill in the art in view of the teachings herein.

To use sterile package system (600), initially medical device (660) is placed within container (672). Primary cover (690) and second cover (680) are then attached to container (672) to seal medical device (660) therein. Second package (670), as constructed, is then sterilized. In one exemplary sterilization technique, second package (670) is placed in a field of radiation that can penetrate second package (670), such as gamma radiation, x-rays, or high-energy electrons. The radiation may kill bacteria on medical device (660) and within second package (670). Second package (670) may alternatively be sterilized using any other technique known in the art, including but not limited to beta or gamma radiation, ethylene oxide, electron beam sterilization, or steam. The sterilized second package (670) may then be stored or shipped to a medical facility for use. Of course, medical device (660) may be sterilized before medical device (660) is placed in container (672), if desired.

For first package (610), initially insertable component (650) is placed within first package (610) without cover (620) attached. First package (610) and insertable component (650) may then be sterilized by electron beam sterilization to limit damage to insertable component (650). Cover (620) is then attached to rim (616) to seal first package (610). The exterior of first package (610), including cover (620), may be sterilized by electron beam sterilization also, though it should be understood that this step is merely optional. Alternatively, if insertable component (650) will not be damaged by penetrating radiation, then fully assembled first package (610) may be placed in a field of radiation that can penetrate first package (610), such as gamma radiation, x-rays, or high-energy electrons. The radiation may kill bacteria on insertable component (650) and within first package (610). First package (610) may alternatively be sterilized using any other technique known in the art, including but not limited to beta or gamma radiation, ethylene oxide, electron beam sterilization, or steam. The sterilized first package (610) containing insertable component (650) may then be stored or shipped to a medical facility for use. Again, insertable component (650) may be sterilized before being placed within first package (610), if desired. In some versions, insertable component (650) is not even sterilized at all.

Figure 9C:
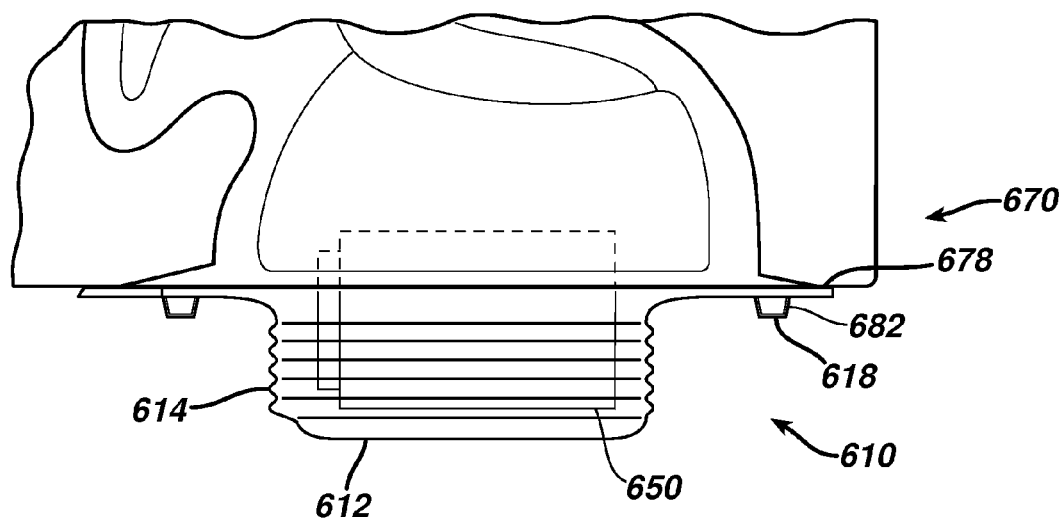
FIG. 9C depicts a side view of the exemplary internal component package of FIG. 9A and medical device package of FIG. 9B, showing the insertion of the non-sterile internal component into the medical device.

Referring to FIGS. 9A-9C, to assemble medical device (660) with insertable component (650) utilizing exemplary sterile package system (600) when medical device (660) is to be used in a medical procedure, initially first package (610) is aligned with second package (670) as shown in FIG. 9B. In the current example, protrusions (682) are inserted into recesses (618). With first package (610) and second package (670) substantially aligned and with first cover (620) and second cover (680) in close proximity, pull tabs (622) and (684) are pulled. Pull tab (622) and pull tab (684) may be pulled either individually or simultaneously by a user. When the pull tabs (622) and (684) are pulled, perforations (624) and (686) detach, respectively. Once first cover (620) and second cover (680) are removed, the interior of first package (610) is in communication with recess (674) of container (672) through opening (676). In some other versions, pull tabs (622, 684) are pulled to remove covers (620, 680) right before protrusions (682) are inserted into recesses (618). In the present example, after protrusions (682) are inserted into recesses (618) and covers (620, 680) are removed, the user then pushes upon base (612) to compress sidewalls (614) and urge insertable component (650) into the cavity (not shown) of medical device (660), as shown in FIG. 9C. Thus, insertable component (650) may be inserted into medical device (660) while still maintaining a substantially sterile environment within both first package (610) and second package (620). Even in instances where insertable component (650) is non-sterile, it should be understood that the configurations of packages (610, 670) and the above-described techniques may prevent insertion of insertable component (650) into medical device (660) without compromising the sterility of medical device (660). Once insertable component (650) is inserted into medical device (660), primary cover (690) is detached and medical device (660) is removed from container (672) for use.

While some exemplary configurations have been described for implementing sterile package system (600) to insert insertable component (650) into medical device (660), various other suitable configurations for sterile packaging system (600) will be apparent to one of ordinary skill in the art in view of the teachings herein.

IV. Cutting Knob for Opening Window into Sterile Packaging to Insert Non-Sterile Components into Medical Device It may alternatively be advantageous to have a substantially closed container that may be cut into to form a window into the interior of a device contained within the closed container. Accordingly, a cutting knob and alignment member attached to the container may be used to provide insertion of non-sterile insertable components into the interior of a medical device (e.g., right before the medical device is to be used). This may also limit the potential for contamination of the exterior of the medical device. The following example relates to an illustrative way in which non-sterile components may be inserted into medical devices while maintaining the sterility of the exterior of the medical device.

A. Package and Medical Device

Figure 11:
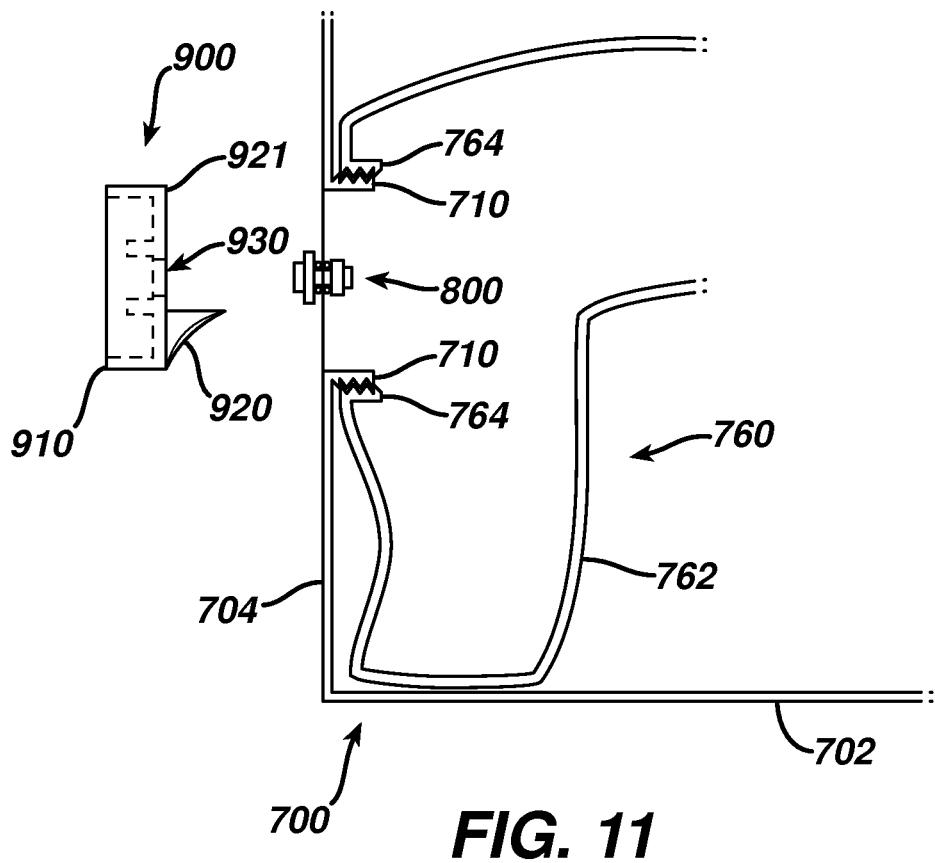
FIG. 11 depicts a partial cross-sectional view of an exemplary sterile package and an exemplary cutting knob for creating a window into the sterile package.

Referring to FIG. 11, an exemplary package (700) is provided for use with a medical device (760) and a cutting knob (900), as will be described later herein. Medical device (760) comprises a housing (762) and device threading (764) and may be constructed at least partially in accordance with at least some of the teachings of medical devices (10), (100), (260), (360), (460), (560), or (660) as previously described herein or medical device (760) may have any other suitable configuration as will be apparent to one of ordinary skill in the art in view of the teachings herein. In the present example, housing (762) defines a rear opening, though it should be understood that the opening in housing (762) may be located at other suitable locations in housing (762) as will be apparent to one of ordinary skill in the art in view of the teachings herein. Housing (762) comprises device threading (764) that encircles the rear opening. Alternative attachment methods, such as those previously described herein, may be implemented with medical device (760) to couple medical device (760) to package (700). While one exemplary configuration for medical device (760) has been described, other suitable configurations for medical device (760) will be apparent to one of ordinary skill in the art in light of the teachings herein.

Package (700) comprises a base (702), a plurality of sidewalls (704), and a cover (not shown). Base (702) and sidewalls (704) in the present example form a homogeneous continuum of material and may be made from a variety of materials including plastics, polyethylene terephthalate glycol (or PETG), other thermoplastic polymer resins, or any other suitable rigid or semi-rigid material. At least one sidewall (704) further comprises attachment member (710) and an opening through which alignment member (800) is disposed, as will be described later herein. Attachment member (710) is configured to couple to medical device (760). Attachment member (710) may be a single continuous protrusion from sidewall (704) or attachment member (710) may comprise a plurality of protrusions from sidewall (704). Additionally, the diameter of attachment member (710) is sized such that an insertable component (not shown) may be inserted through the diameter of attachment member (710) once a hole is formed by cutting knob (900). In the present example, attachment member (710) comprises a cylindrical protrusion threaded to complement device threading (764). Alternatively, attachment member (710) may comprise a protrusion to mechanically snap-on or friction fit with medical device (760) to secure medical device (760) within package (700). Further still, attachment member (710) may be omitted and medical device (760) may be adhesively attached to sidewall (704) or otherwise be fixedly yet removably positioned adjacent to sidewall.

In the example shown in FIG. 11, medical device (760) is initially coupled to attachment member (710) to secure medical device (760) within package (700). With alignment member (800) disposed in sidewall (704) and cover (not shown) attached to package (700), package (700) is sterilized. In one exemplary sterilization technique, package (700) is placed in a field of radiation that can penetrate package (700), such as gamma radiation, x-rays, or high-energy electrons. The radiation may kill bacteria on medical device (760) and within package (700). Package (700) containing medical device (760) may alternatively be sterilized using any other technique known in the art, including but not limited to beta or gamma radiation, ethylene oxide, electron beam sterilization, or steam. The sterilized package (700) containing medical device (760) may then be stored or shipped to a medical facility for use. It should also be understood that medical device (760) may be sterilized before being placed in package (700).

While an exemplary configuration of package (700) has been described, various other suitable configurations for package (700) may be provided as will be apparent to one of ordinary skill in the art in view of the teachings herein.

B. Alignment Member

Figure 12:
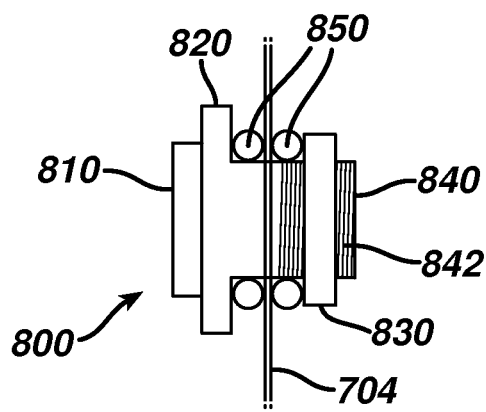
FIG. 12 depicts a partial cross-sectional view of the alignment member of FIG. 11 attached to the wall of a sterile package.

FIG. 12 shows alignment member (800) disposed through sidewall (704) of package (700). Alignment member (800) of the present example comprises a key (810), an exterior portion (820), a body portion (840), and an interior retention member (830). Body portion (840) further comprises threading (842) onto which interior retention member (830) may couple to body portion (840). Alignment member (800) may be made from a variety of rigid materials including, but not limited to, metals, metal alloys, plastics, thermoplastic polymers, or any other suitable rigid material as will be apparent to those of ordinary skill in the art in view of the teachings herein. In the current example, alignment member (800) is a threaded plastic bolt having a key (810) extending from the exterior portion (820) of alignment member (800). Key (810) of the present example is a cylindraceous protrusion that is insertable into alignment recess (930) of cutting knob (900) as will be described herein. Interior retention member (830) of the present example is a complementary nut to the threaded plastic bolt. In one exemplary alternative, interior retention member (830) may be adhesively attached to body portion (840) after insertion of alignment member (800) into sidewall (704). In yet another alternative arrangement, interior retention member (830) may further comprise a set screw (not shown) to secure interior retention member (830) to body portion (840).

Alignment member (800) may further comprise a seal (850) or a plurality of seals (850), as shown in FIG. 12, though it should be understood that seal (850) is merely optional. Seal (850) is configured to substantially conform to the size and shape of body portion (840) of alignment member (800). Seal (850) may be made from a variety of materials, including natural rubber, silicone, neoprene, Polytetrafluoroethylene (or PTFE), or other suitable sealing materials as will be apparent to those of ordinary skill in the art in view of the teachings herein. In the present example, seal (850) is an o-ring type seal. When alignment member (800) of the present example is inserted into sidewall (704) of package (700) and interior retention member (830) is attached, exterior portion (820) compresses a first seal (850) against sidewall (704) on the exterior of package (700) to hermetically seal the exterior of alignment member (800) to sidewall (704). If a second seal is provided, interior retention member (830) may compress second seal (850) against sidewall (704) on the interior of package (700) to hermetically seal the interior of alignment member (800) to sidewall (704). Thus, when alignment member (800) is used with package (700) in sidewall (704), the sterility within package (700) may be maintained after medical device (760) and package (700) undergo sterilization. Various other suitable configurations for seal (850) will be apparent to one of ordinary skill in the art in view of the teachings herein.

While an exemplary configuration for alignment member (800) has been described, various other suitable configurations for alignment (800) may be provided as will be apparent to one of ordinary skill in the art in view of the teachings herein.

C. Cutting Knob

Cutting knob (900) of the present example comprises a handle member (910), a knife (920), and an alignment recess (930). In the present configuration, handle member (910) is a circular rotatable knob configured to be grasped by a user and rotated when cutting knob (900) is coupled to alignment member (800). Knife (920) is attached to and protrudes from handle member (910) and is configured to pierce and cut through sidewall (704) of container (700). In the present example, knife (920) is formed by a curved, sharp portion of metal located near the perimeter of handle member (910). Knife (920) is positioned on handle member (910) such that when knife (920) is rotated, the circular diameter of the opening formed by knife (920) when cutting through sidewall (704) of package (700) is no larger than the diameter formed by attachment member (710), as previously described herein, and such that an insertable component (not shown) may be inserted through that hole and into medical device (760). In some versions, the entire distal edge (921) of cutting knob (900) presents a sharp annular edge, such that a separately protruding knife (920) is not necessary. As yet another merely illustrative variation, distal edge (921) may be serrated with a sawtooth configuration to facilitate cutting of a circular opening through sidewall (704) of package (700).

Handle member (910) further comprises an alignment recess (930) into which a key (810) of alignment member (800) may be inserted. In the present example, alignment recess (930) is shown as a circular opening, but it should be understood that alignment recess may be configured for a variety of shapes, including stars, hexagons, rectangles, triangles, or any other suitable shape as will be apparent to one of ordinary skill in the art in light of the teachings herein.

While an exemplary configuration for cutting knob (900) has been described, various other suitable configurations for cutting knob (900) may be provided as will be apparent to one of ordinary skill in the art in view of the teachings herein.

D. Operation of Cutting Knob

Figure 13:
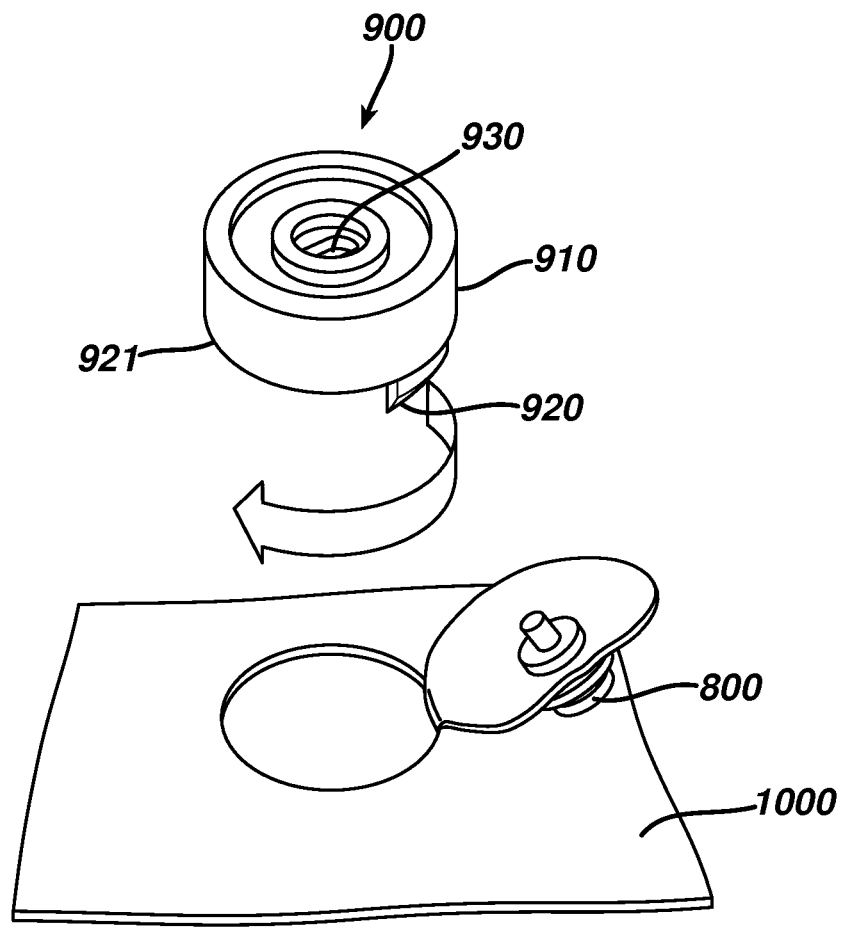
FIG. 13 depicts a perspective view of the operation of the exemplary cutting knob of FIG. 11 and a resulting window in a sterile package.

FIG. 13 depicts an exemplary implementation of cutting knob (900) to form an opening in an exemplary wall (1000). Wall (1000) may be constructed in accordance with at least some of the teachings pertaining to sidewall (704) as shown in FIG. 11, or wall (1000) may correspond to any other suitable portion of a package previously described herein, including insertion package (200), insertion package (400), or package (700). Initially, the user aligns alignment recess (930) of cutting knob (900) with key (810) of alignment member (800). The user pushes cutting knob (900) against wall (1000) causing knife (920) to pierce wall (1000). The user then rotates cutting knob (900) to complete a revolution, thereby detaching a circular portion of wall (1000) and permitting access through the opening formed. Alternatively, the user may stop just prior to completing a full revolution, thereby leaving a portion of wall (1000) attached and allowing the user to pull back the substantially detached portion.

Referring back to FIG. 11, if cutting knob (900) is used accordingly with sidewall (704), then the opening formed may permit access only into the interior of medical device (760), thereby potentially maintaining the sterility of the exterior of medical device (760) and the interior of package (700). A non-sterile insertable component (not shown) may then be inserted into medical device (760) while preventing or reducing the risk of potential contamination of other components still encased within package (700). The cover (not shown) of package (700) may then be removed to permit use of medical device (760) for a procedure.

While an exemplary implementation of package (700), medical device (760), cutting knob (900), and alignment member (800) has been described, various other suitable implementations will be apparent to one of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system for insertion of insertable components into a medical device, the system comprising:
   (a) a container, wherein the container defines an interior; and
   (b) a medical device sealed within the interior of the container;
   (c) a electrical component wherein the electrical component comprises a portable power source or an ultrasonic transducer;
   wherein the exterior of the medical device and the interior of the container are sterile;
   wherein the medical device comprises an interior cavity, wherein the interior cavity is configured to receive the electrical component;
   wherein the container defines an opening configured to permit selective insertion of the electrical component into the interior cavity of the medical device while the medical device is within the container and without compromising the sterility of the exterior of the medical device; and
   wherein the medical device is removable from the container with the electrical component disposed in the cavity.

2. The system of claim 1, wherein the container comprises a base and a plurality of sidewalls extending from the base, wherein the opening is defined in one of the sidewalls, the system further comprising:
   (a) a first cover detachably secured relative to the plurality of sidewalls;
   (b) an attachment member, wherein the attachment member is coupled to the sidewall defining the opening, wherein the attachment member defines an opening corresponding to the opening formed through the sidewall; and
   (c) a second cover detachably attached to an exterior surface of the sidewall defining the opening;
   wherein the opening of the sidewall and the opening of the attachment member are configured to permit the electrical component to be inserted therethrough and into the medical device.

3. The system of claim 2, wherein the attachment member comprises:
   (i) a cylindraceous portion having first end and a second end, wherein the cylindraceous portion is disposed through the opening of the sidewall,
   (ii) a rim extending outwardly from the first end of the cylindraceous portion, wherein the rim is configured to abut against the exterior surface of the sidewall defining the opening, and
   (iii) threading formed on an exterior portion of the second end of the cylindraceous portion.

4. The system of claim 3, wherein the medical device includes threading, wherein the threading of the cylindraceous portion is configured to complement the threading of the medical device.

5. The system of claim 2, wherein the sidewall defining the opening further comprises a retention feature protruding from the exterior surface of the sidewall, wherein the retention feature is configured to restrict movement of the attachment member relative to the sidewall defining the opening.

6. The system of claim 5, wherein the attachment member comprises a retention portion, an attachment portion, and a cylindraceous portion, wherein the retention portion is configured to couple with the retention feature.

7. The system of claim 6, wherein the medical device includes interior threading, wherein the attachment portion comprises exterior threading configured to complement the interior threading of the medical device, wherein the exterior threading of the attachment portion is formed on an exterior surface of the attachment portion.

8. The system of claim 7, wherein the attachment member is configured to deflect atleast part of the attachment portion inwardly when the retention portion is squeezed.

9. The system of claim 5, wherein the retention feature permits rotation of the attachment member relative to the sidewall defining the opening while restricting movement of the attachment member relative to the sidewall defining the opening along an axis defined by the attachment member.

10. A system for insertion of insertable components into a medical device, the system comprising:
    (a) a container defines an interior;
    (b) an ultrasonic surgical instrument sealed within the interior of the container; and
    (c) a ultrasonic transducer;
    wherein the exterior of the ultrasonic surgical instrument and the interior of the container are sterile;
    wherein the ultrasonic surgical instrument comprises an interior cavity, wherein the interior cavity is configured to receive the ultrasonic transducer;
    wherein the container defines an opening configured to permit selective insertion of the transducer into the interior cavity of the ultrasonic surgical instrument while the ultrasonic surgical instrument is within the container and without compromising the sterility of the exterior of the ultrasonic surgical instrument; and
    wherein the ultrasonic surgical instrument is removable from the container with the transducer disposed in the cavity.

11. A system for insertion of insertable components into a medical device, the system compromising:
    (a) a container, wherein the container defines an interior (b) a powered surgical instrument sealed within the interior of the container, wherein the powered surgical instrument includes an end effector having an active; and
(c) a portable power source, wherein the powered surgical instrument is operable to drive the active element of the end effector using power from the portable power source;
wherein the exterior of the powered surgical instrument and the interior of the container are sterile;
wherein the powered surgical instrument comprises an interior cavity, wherein the interior cavity is configured to receive the portable power source;
wherein the container defines an opening configured to permit selective insertion of the potable power device into the interior cavity of the powered surgical instrument while the powered surgical instrument is within the container and without compromising the sterility of the powered surgical instrument; and
wherein the powered surgical instrument is removable from the container with the portable device disposed in the cavity.

* * * * *